United States Patent
Mauldin et al.

(10) Patent No.: US 11,980,377 B2
(45) Date of Patent: May 14, 2024

(54) PATIENT SPECIFIC INSTRUMENTS AND METHODS FOR JOINT PROSTHESIS

(71) Applicant: Howmedica Osteonics Corp., Mahwah, NJ (US)

(72) Inventors: Richard Garret Mauldin, Erie, CO (US); Thomas Anthony Flanagan, Bloomington, MN (US); Emmanuel Francois Marie Lizee, St. Ismier (FR)

(73) Assignee: HOWMEDICA OSTEONICS CORP., Mahwah, NJ (US)

( * ) Notice: Subject to any disclaimer, the term of this patent is extended or adjusted under 35 U.S.C. 154(b) by 304 days.

(21) Appl. No.: 17/348,993

(22) Filed: Jun. 16, 2021

(65) Prior Publication Data
US 2021/0315593 A1  Oct. 14, 2021

Related U.S. Application Data

(63) Continuation of application No. 16/008,471, filed on Jun. 14, 2018, now Pat. No. 11,065,016, which is a
(Continued)

(51) Int. Cl.
*A61B 17/17* (2006.01)
*A61B 17/15* (2006.01)
(Continued)

(52) U.S. Cl.
CPC .......... *A61B 17/1775* (2016.11); *A61B 17/15* (2013.01); *A61B 34/10* (2016.02);
(Continued)

(58) Field of Classification Search
CPC ..... A61B 17/17; A61B 17/1775; A61B 17/15; A61B 17/56; A61B 17/90; A61B 34/10
See application file for complete search history.

(56) References Cited

U.S. PATENT DOCUMENTS

| | | |
|---|---|---|
| 4,919,670 A | 4/1990 | Dale et al. |
| 5,030,219 A | 7/1991 | Matsen, III et al. |
| | (Continued) | |

FOREIGN PATENT DOCUMENTS

| | | |
|---|---|---|
| CA | 2927086 | 4/2015 |
| CA | 2927811 | 4/2015 |
| | (Continued) | |

OTHER PUBLICATIONS

US 9,451,972 B2, 09/2016, Lang et al. (withdrawn)
(Continued)

*Primary Examiner* — Christopher J Beccia
(74) *Attorney, Agent, or Firm* — DUANE MORRIS LLP

(57) ABSTRACT

A system for preparing an ankle bone to receive an ankle prosthesis is provided. The system includes a patient specific cutting guide that has an anterior surface, a posterior surface, and at least one cutting feature extending through the guide from the anterior surface. The posterior surface comprising a first protrusion or other member that extends from a first end fixed to the posterior surface to a second end disposed away from the first end of the first protrusion. The posterior surface has a second protrusion or other member that extends from a first end fixed to the posterior surface to a second end disposed away from the first end of the second protrusion. The first and second protrusions are spaced apart and have a length such that when the patient specific cutting guide is coupled with first and second bone references, which can include bushings implantable in bones, a clearance gap is provided between the posterior surface and the ankle bone.

23 Claims, 19 Drawing Sheets

Related U.S. Application Data continuation of application No. PCT/US2016/063883, filed on Nov. 28, 2016.

(60) Provisional application No. 62/268,045, filed on Dec. 16, 2015.

(51) Int. Cl.
*A61B 34/10* (2016.01)
*A61B 17/56* (2006.01)
*A61B 17/90* (2006.01)

(52) U.S. Cl.
CPC ......... *A61B 2017/568* (2013.01); *A61B 17/90* (2021.08); *A61B 2034/105* (2016.02); *A61B 2034/108* (2016.02)

(56) References Cited

U.S. PATENT DOCUMENTS

| | | | |
|---|---|---|---|
| 5,329,846 A | 7/1994 | Bonutti | |
| 5,383,938 A | 1/1995 | Rohr et al. | |
| 5,458,637 A | 10/1995 | Hayes | |
| 5,531,793 A | 7/1996 | Kelman et al. | |
| 5,610,966 A | 3/1997 | Martell et al. | |
| 5,725,586 A | 3/1998 | Sommerich | |
| 5,768,134 A | 6/1998 | Swaelens et al. | |
| 5,769,856 A | 6/1998 | Dong et al. | |
| 5,779,710 A | 7/1998 | Matsen, III | |
| 5,807,437 A | 9/1998 | Sachs et al. | |
| 5,824,078 A | 10/1998 | Nelson et al. | |
| 5,824,085 A | 10/1998 | Sahay et al. | |
| 6,002,859 A | 12/1999 | DiGioia, III et al. | |
| 6,129,764 A | 10/2000 | Servidio | |
| 6,172,856 B1 | 1/2001 | Jang | |
| 6,364,910 B1 | 4/2002 | Shultz et al. | |
| 6,385,475 B1 | 5/2002 | Cinquin et al. | |
| 6,432,142 B1 | 8/2002 | Kamiya et al. | |
| 6,459,948 B1 | 10/2002 | Ateshian et al. | |
| 6,648,894 B2 | 11/2003 | Abdelgany et al. | |
| 6,772,026 B2 | 8/2004 | Bradbury et al. | |
| 6,797,006 B2 | 9/2004 | Hodorek | |
| 6,849,223 B2 | 2/2005 | Dean et al. | |
| 6,915,150 B2 | 7/2005 | Cinquin et al. | |
| 6,944,518 B2 | 9/2005 | Roose | |
| 7,175,665 B2 | 2/2007 | German et al. | |
| 7,468,075 B2 | 12/2008 | Lang et al. | |
| 7,469,474 B2 | 12/2008 | Farrar | |
| 7,534,263 B2 | 5/2009 | Burdulis, Jr. et al. | |
| 7,599,539 B2 | 10/2009 | Kunz et al. | |
| 7,618,451 B2 | 11/2009 | Berez et al. | |
| 7,634,119 B2 | 12/2009 | Tsougarakis et al. | |
| 7,648,530 B2 | 1/2010 | Habermeyer et al. | |
| 7,678,150 B2 | 3/2010 | Tornier et al. | |
| 7,702,380 B1 | 4/2010 | Dean | |
| 7,717,956 B2 | 5/2010 | Lang | |
| 7,747,305 B2 | 6/2010 | Dean et al. | |
| 7,796,791 B2 | 9/2010 | Tsougarakis et al. | |
| 7,799,077 B2 | 9/2010 | Lang et al. | |
| 7,802,503 B2 | 9/2010 | Couvillion et al. | |
| 7,822,588 B2 | 10/2010 | Mueller et al. | |
| 7,831,079 B2 | 11/2010 | Kunz et al. | |
| 7,892,287 B2 | 2/2011 | Deffenbaugh | |
| 7,927,338 B2 | 4/2011 | Laffargue et al. | |
| 7,981,158 B2 | 7/2011 | Fitz et al. | |
| 7,983,777 B2 | 7/2011 | Melton et al. | |
| 7,993,408 B2 | 8/2011 | Meridew et al. | |
| 8,007,448 B2 | 8/2011 | Barrera | |
| 8,014,984 B2 | 9/2011 | Iannotti et al. | |
| 8,055,487 B2 | 11/2011 | James | |
| 8,062,302 B2 | 11/2011 | Lang et al. | |
| 8,066,708 B2 | 11/2011 | Lang et al. | |
| 8,077,950 B2 | 12/2011 | Tsougarakis et al. | |
| 8,083,745 B2 | 12/2011 | Lang et al. | |
| 8,094,900 B2 | 1/2012 | Steines et al. | |
| 8,105,330 B2 | 1/2012 | Fitz et al. | |
| 8,122,582 B2 | 2/2012 | Burdulis, Jr. et al. | |
| 8,234,097 B2 | 7/2012 | Steines et al. | |
| 8,337,501 B2 | 12/2012 | Fitz et al. | |
| 8,337,507 B2 | 12/2012 | Lang et al. | |
| 8,343,218 B2 | 1/2013 | Lang et al. | |
| 8,350,186 B2 | 1/2013 | Jones et al. | |
| 8,366,771 B2 | 2/2013 | Burdulis, Jr. et al. | |
| 8,377,073 B2 | 2/2013 | Wasielewski | |
| 8,377,129 B2 | 2/2013 | Fitz et al. | |
| 8,439,926 B2 | 5/2013 | Bojarski et al. | |
| 8,457,930 B2 | 6/2013 | Schroeder | |
| 8,460,304 B2 | 6/2013 | Fitz et al. | |
| 8,480,754 B2 | 7/2013 | Bojarski et al. | |
| 8,500,740 B2 | 8/2013 | Bojarski et al. | |
| 8,529,568 B2 | 9/2013 | Bouadi | |
| 8,529,630 B2 | 9/2013 | Bojarski et al. | |
| 8,532,806 B1 | 9/2013 | Masson | |
| 8,535,319 B2 | 9/2013 | Ball | |
| 8,545,509 B2 | 10/2013 | Park et al. | |
| 8,545,569 B2 | 10/2013 | Fitz et al. | |
| 8,551,099 B2 | 10/2013 | Lang et al. | |
| 8,551,102 B2 | 10/2013 | Fitz et al. | |
| 8,551,103 B2 | 10/2013 | Fitz et al. | |
| 8,551,169 B2 | 10/2013 | Fitz et al. | |
| 8,556,906 B2 | 10/2013 | Fitz et al. | |
| 8,556,907 B2 | 10/2013 | Fitz et al. | |
| 8,556,971 B2 | 10/2013 | Lang | |
| 8,556,983 B2 | 10/2013 | Bojarski et al. | |
| 8,561,278 B2 | 10/2013 | Fitz et al. | |
| 8,562,611 B2 | 10/2013 | Fitz et al. | |
| 8,562,618 B2 | 10/2013 | Fitz et al. | |
| 8,568,479 B2 | 10/2013 | Fitz et al. | |
| 8,568,480 B2 | 10/2013 | Fitz et al. | |
| 8,585,708 B2 | 11/2013 | Fitz et al. | |
| 8,608,749 B2 | 12/2013 | Meridew et al. | |
| 8,617,172 B2 | 12/2013 | Fitz et al. | |
| 8,617,242 B2 | 12/2013 | Philipp | |
| 8,623,026 B2 | 1/2014 | Wong et al. | |
| 8,634,617 B2 | 1/2014 | Tsougarakis et al. | |
| 8,638,998 B2 | 1/2014 | Steines et al. | |
| 8,641,716 B2 | 2/2014 | Fitz et al. | |
| 8,657,827 B2 | 2/2014 | Fitz et al. | |
| 8,663,333 B2 | 3/2014 | Metcalfe et al. | |
| 8,682,052 B2 | 3/2014 | Fitz et al. | |
| 8,690,945 B2 | 4/2014 | Fitz et al. | |
| 8,709,089 B2 | 4/2014 | Lang et al. | |
| 8,731,885 B2 | 5/2014 | Iannotti et al. | |
| 8,735,773 B2 | 5/2014 | Lang | |
| 8,744,148 B2 | 6/2014 | Nord et al. | |
| 8,768,028 B2 | 7/2014 | Lang et al. | |
| 8,771,365 B2 | 7/2014 | Bojarski et al. | |
| 8,774,900 B2 | 7/2014 | Buly et al. | |
| 8,775,133 B2 | 7/2014 | Schroeder | |
| 8,781,557 B2 | 7/2014 | Dean et al. | |
| 8,814,942 B2 | 8/2014 | Anthony et al. | |
| 8,843,229 B2 | 9/2014 | Vanasse et al. | |
| 8,864,769 B2 | 10/2014 | Stone et al. | |
| 8,882,847 B2 | 11/2014 | Burdulis, Jr. et al. | |
| 8,884,618 B2 | 11/2014 | Mahfouz | |
| 8,888,855 B2 | 11/2014 | Roche et al. | |
| 8,898,043 B2 | 11/2014 | Ashby et al. | |
| 8,906,107 B2 | 12/2014 | Bojarski et al. | |
| 8,926,706 B2 | 1/2015 | Bojarski et al. | |
| 8,932,361 B2 | 1/2015 | Tornier et al. | |
| 8,932,363 B2 | 1/2015 | Tsougarakis et al. | |
| 8,934,961 B2 | 1/2015 | Lakin et al. | |
| 8,945,230 B2 | 2/2015 | Lang et al. | |
| 8,951,259 B2 | 2/2015 | Fitz et al. | |
| 8,951,260 B2 | 2/2015 | Lang et al. | |
| 8,965,088 B2 | 2/2015 | Tsougarakis et al. | |
| 8,971,606 B2 | 3/2015 | Chaoui | |
| 8,974,539 B2 | 3/2015 | Bojarski et al. | |
| 8,984,731 B2 | 3/2015 | Broeck et al. | |
| 8,989,460 B2 | 3/2015 | Mahfouz | |
| 8,992,538 B2 | 3/2015 | Keefer | |
| 8,998,915 B2 | 4/2015 | Fitz et al. | |
| 9,020,788 B2 | 4/2015 | Lang | |
| 9,023,050 B2 | 5/2015 | Lang et al. | |
| 9,055,953 B2 | 6/2015 | Lang et al. | |

(56) References Cited

U.S. PATENT DOCUMENTS

| | | |
|---|---|---|
| 9,060,788 B2 | 6/2015 | Bollinger |
| 9,066,728 B2 | 6/2015 | Burdulis, Jr. et al. |
| 9,072,531 B2 | 7/2015 | Fitz et al. |
| 9,084,617 B2 | 7/2015 | Lang et al. |
| 9,095,353 B2 | 8/2015 | Burdulis, Jr. et al. |
| 9,107,679 B2 | 8/2015 | Lang et al. |
| 9,107,680 B2 | 8/2015 | Fitz et al. |
| 9,113,921 B2 | 8/2015 | Lang et al. |
| 9,125,672 B2 | 9/2015 | Fitz et al. |
| 9,126,673 B1 | 9/2015 | Green et al. |
| 9,180,015 B2 | 11/2015 | Fitz et al. |
| 9,186,161 B2 | 11/2015 | Lang et al. |
| 9,186,254 B2 | 11/2015 | Fitz et al. |
| 9,208,558 B2 | 12/2015 | Dean et al. |
| 9,211,199 B2 | 12/2015 | Ratron |
| 9,216,025 B2 | 12/2015 | Fitz et al. |
| 9,220,516 B2 | 12/2015 | Lang et al. |
| 9,220,517 B2 | 12/2015 | Lang et al. |
| 9,232,955 B2 | 1/2016 | Bonin, Jr. et al. |
| 9,237,950 B2 | 1/2016 | Hensley et al. |
| 9,241,724 B2 | 1/2016 | Lang et al. |
| 9,241,725 B2 | 1/2016 | Lang et al. |
| 9,275,191 B2 | 3/2016 | Dean et al. |
| 9,278,413 B2 | 3/2016 | Sperling |
| 9,292,920 B2 | 3/2016 | Dean et al. |
| 9,295,481 B2 | 3/2016 | Fitz et al. |
| 9,295,482 B2 | 3/2016 | Fitz et al. |
| 9,301,768 B2 | 4/2016 | Buza et al. |
| 9,308,005 B2 | 4/2016 | Fitz et al. |
| 9,308,053 B2 | 4/2016 | Bojarski et al. |
| 9,308,091 B2 | 4/2016 | Lang |
| 9,314,256 B2 | 4/2016 | Fitz et al. |
| 9,320,608 B2 | 4/2016 | Sperling |
| 9,320,620 B2 | 4/2016 | Bojarski et al. |
| 9,326,780 B2 | 5/2016 | Wong et al. |
| 9,326,862 B2 | 5/2016 | Smith et al. |
| 9,330,206 B2 | 5/2016 | Dean et al. |
| 9,333,085 B2 | 5/2016 | Fitz et al. |
| 9,351,743 B2 | 5/2016 | Kehres et al. |
| 9,358,018 B2 | 6/2016 | Fitz et al. |
| 9,381,025 B2 | 7/2016 | Fitz et al. |
| 9,381,026 B2 | 7/2016 | Trouilloud et al. |
| 9,387,083 B2 | 7/2016 | Al Hares et al. |
| 9,402,726 B2 | 8/2016 | Linderman et al. |
| 9,408,615 B2 | 8/2016 | Fitz et al. |
| 9,408,616 B2 | 8/2016 | Kehres et al. |
| 9,408,686 B1 | 8/2016 | Miller et al. |
| 9,414,928 B2 | 8/2016 | Sperling |
| 9,439,767 B2 | 9/2016 | Bojarski et al. |
| 9,486,226 B2 | 11/2016 | Chao |
| 9,495,483 B2 | 11/2016 | Steines et al. |
| 9,498,344 B2 | 11/2016 | Hodorek et al. |
| 9,517,134 B2 | 12/2016 | Lang |
| 9,539,013 B2 | 1/2017 | Katrana et al. |
| 9,554,910 B2 | 1/2017 | Vanasse et al. |
| 9,575,931 B2 | 2/2017 | Ratron |
| 9,579,106 B2 | 2/2017 | Lo et al. |
| 9,579,110 B2 | 2/2017 | Bojarski et al. |
| 9,603,711 B2 | 3/2017 | Bojarski et al. |
| 9,626,756 B2 | 4/2017 | Dean et al. |
| 9,636,229 B2 | 5/2017 | Lang et al. |
| 9,646,113 B2 | 5/2017 | Park et al. |
| 9,662,214 B2 | 5/2017 | Li et al. |
| 9,668,873 B2 | 6/2017 | Winslow et al. |
| 9,672,302 B2 | 6/2017 | Dean et al. |
| 9,672,617 B2 | 6/2017 | Dean et al. |
| 9,675,471 B2 | 6/2017 | Bojarski et al. |
| 9,681,956 B2 | 6/2017 | Al Hares et al. |
| 9,687,945 B2 | 6/2017 | Steines et al. |
| 9,700,420 B2 | 7/2017 | Fitz et al. |
| 9,700,971 B2 | 7/2017 | Lang |
| 9,713,533 B2 | 7/2017 | Taylor et al. |
| 9,715,563 B1 | 7/2017 | Schroeder |
| 9,717,508 B2 | 8/2017 | Iannotti et al. |
| 9,737,367 B2 | 8/2017 | Steines et al. |
| 9,741,263 B2 | 8/2017 | Iannotti et al. |
| 9,770,335 B2 | 9/2017 | Sperling |
| 9,775,680 B2 | 10/2017 | Bojarski et al. |
| 9,849,019 B2 | 12/2017 | Miller et al. |
| 9,872,773 B2 | 1/2018 | Lang et al. |
| 9,877,790 B2 | 1/2018 | Bojarski et al. |
| 9,895,230 B2 | 2/2018 | Mahfouz |
| 9,913,723 B2 | 3/2018 | Fitz et al. |
| 9,937,046 B2 | 4/2018 | Mahfouz |
| 9,943,370 B2 | 4/2018 | Asseln et al. |
| 9,956,047 B2 | 5/2018 | Bojarski et al. |
| 9,956,048 B2 | 5/2018 | Bojarski et al. |
| 9,993,341 B2 | 6/2018 | Vanasse et al. |
| 10,068,671 B2 | 9/2018 | Dean et al. |
| 10,085,839 B2 | 10/2018 | Wong et al. |
| 10,405,993 B2 | 9/2019 | Deransart et al. |
| 10,433,969 B2 | 10/2019 | Humphrey |
| 10,548,737 B2 | 2/2020 | Hodorek et al. |
| 10,716,676 B2 | 7/2020 | Tornier et al. |
| 11,065,016 B2 * | 7/2021 | Mauldin ................ A61B 17/15 |
| 11,364,127 B2 | 6/2022 | Deransart et al. |
| 2001/0047210 A1 | 11/2001 | Wolf |
| 2002/0007294 A1 | 1/2002 | Bradbury et al. |
| 2002/0025358 A1 | 2/2002 | Nelson et al. |
| 2002/0082741 A1 | 6/2002 | Mazumder et al. |
| 2003/0139818 A1 | 7/2003 | Rogers et al. |
| 2004/0064189 A1 | 4/2004 | Maroney et al. |
| 2004/0102866 A1 | 5/2004 | Harris et al. |
| 2004/0133276 A1 | 7/2004 | Lang et al. |
| 2004/0171924 A1 | 9/2004 | Mire et al. |
| 2004/0181144 A1 | 9/2004 | Cinquin et al. |
| 2004/0199258 A1 | 10/2004 | Macara |
| 2004/0243481 A1 | 12/2004 | Bradbury et al. |
| 2005/0049709 A1 | 3/2005 | Tornier |
| 2005/0065617 A1 | 3/2005 | Barrera et al. |
| 2005/0065628 A1 | 3/2005 | Roose |
| 2005/0112397 A1 | 5/2005 | Rolfe et al. |
| 2005/0197814 A1 | 9/2005 | Aram |
| 2005/0216305 A1 | 9/2005 | Funderud |
| 2006/0100714 A1 | 5/2006 | Ensign |
| 2006/0136058 A1 | 6/2006 | Pietrzak |
| 2006/0161167 A1 | 7/2006 | Myers et al. |
| 2007/0089518 A1 | 4/2007 | Ericson et al. |
| 2007/0118055 A1 | 5/2007 | McCombs |
| 2007/0118243 A1 | 5/2007 | Schroeder et al. |
| 2007/0173945 A1 | 7/2007 | Wiley et al. |
| 2007/0191741 A1 | 8/2007 | Tsai et al. |
| 2007/0244563 A1 | 10/2007 | Roche et al. |
| 2007/0249967 A1 | 10/2007 | Buly et al. |
| 2008/0014082 A1 | 1/2008 | Kunz et al. |
| 2008/0109000 A1 | 5/2008 | Maroney et al. |
| 2008/0140209 A1 | 6/2008 | Iannotti et al. |
| 2008/0183297 A1 | 7/2008 | Boileau et al. |
| 2008/0228269 A1 | 9/2008 | McLeod et al. |
| 2008/0243127 A1 | 10/2008 | Lang et al. |
| 2009/0099662 A1 | 4/2009 | Splieth et al. |
| 2009/0204225 A1 | 8/2009 | Meridew et al. |
| 2009/0226068 A1 | 9/2009 | Fitz et al. |
| 2009/0264894 A1 | 10/2009 | Wasielewski |
| 2009/0292464 A1 | 11/2009 | Fuchs et al. |
| 2010/0082035 A1 | 4/2010 | Keefer |
| 2010/0087927 A1 | 4/2010 | Roche et al. |
| 2010/0161066 A1 | 6/2010 | Iannotti et al. |
| 2010/0191100 A1 | 7/2010 | Anderson et al. |
| 2010/0217270 A1 | 8/2010 | Polinski et al. |
| 2010/0303313 A1 | 12/2010 | Lang et al. |
| 2011/0029088 A1 | 2/2011 | Raucher et al. |
| 2011/0040334 A1 | 2/2011 | Kaes et al. |
| 2011/0046735 A1 | 2/2011 | Metzger et al. |
| 2011/0054478 A1 | 3/2011 | Vanasse et al. |
| 2011/0119884 A1 | 5/2011 | Ratron |
| 2011/0144760 A1 | 6/2011 | Wong et al. |
| 2011/0282403 A1 | 11/2011 | Anthony et al. |
| 2012/0078258 A1 | 3/2012 | Lo et al. |
| 2012/0116203 A1 | 5/2012 | Vancraen et al. |
| 2012/0130434 A1 * | 5/2012 | Stemniski .......... A61B 17/1775 |
| | | 606/86 R |
| 2012/0141034 A1 | 6/2012 | Iannotti et al. |
| 2012/0143267 A1 | 6/2012 | Iannotti et al. |

(56) References Cited

U.S. PATENT DOCUMENTS

| | | |
|---|---|---|
| 2012/0221112 A1 | 8/2012 | Lappin |
| 2012/0232670 A1 | 9/2012 | Bojarski et al. |
| 2012/0253350 A1 | 10/2012 | Anthony et al. |
| 2012/0253467 A1 | 10/2012 | Frankle |
| 2012/0276509 A1 | 11/2012 | Iannotti et al. |
| 2012/0279933 A1 | 11/2012 | Hensler et al. |
| 2012/0296339 A1 | 11/2012 | Iannotti et al. |
| 2013/0053968 A1 | 2/2013 | Nardini et al. |
| 2013/0110116 A1 | 5/2013 | Kehres et al. |
| 2013/0110470 A1 | 5/2013 | Vanasse et al. |
| 2013/0110471 A1 | 5/2013 | Lang et al. |
| 2013/0114873 A1 | 5/2013 | Chaoui |
| 2013/0150975 A1 | 6/2013 | Iannotti et al. |
| 2013/0172898 A1 | 7/2013 | Iannotti et al. |
| 2013/0190882 A1 | 7/2013 | Humphrey |
| 2013/0204375 A1 | 8/2013 | Winslow et al. |
| 2013/0211531 A1 | 8/2013 | Steines et al. |
| 2013/0261629 A1 | 10/2013 | Anthony et al. |
| 2013/0274752 A1 | 10/2013 | Trouilloud et al. |
| 2013/0325134 A1 | 12/2013 | Viscardi et al. |
| 2013/0338673 A1 | 12/2013 | Keppler |
| 2014/0039633 A1 | 2/2014 | Roche et al. |
| 2014/0074246 A1 | 3/2014 | Huebner et al. |
| 2014/0236304 A1 | 8/2014 | Hodorek et al. |
| 2014/0257499 A1 | 9/2014 | Winslow et al. |
| 2014/0276867 A1 | 9/2014 | Kelley et al. |
| 2014/0371863 A1 | 12/2014 | Vanasse et al. |
| 2015/0045903 A1 | 2/2015 | Neal |
| 2015/0054195 A1 | 2/2015 | Greyf |
| 2015/0093283 A1 | 4/2015 | Miller et al. |
| 2015/0105787 A1 | 4/2015 | Tornier et al. |
| 2015/0150688 A1 | 6/2015 | Vanasse et al. |
| 2015/0190151 A1 | 7/2015 | Budhabhatti et al. |
| 2015/0202045 A1 | 7/2015 | Early et al. |
| 2015/0223941 A1 | 8/2015 | Lang |
| 2015/0250552 A1 | 9/2015 | Radermacher et al. |
| 2015/0250597 A1 | 9/2015 | Lang et al. |
| 2015/0265411 A1 | 9/2015 | Deransart et al. |
| 2015/0320430 A1 | 11/2015 | Kehres et al. |
| 2015/0328004 A1 | 11/2015 | Mafhouz |
| 2016/0015466 A1 | 1/2016 | Park et al. |
| 2016/0051367 A1 | 2/2016 | Gervasi et al. |
| 2016/0067049 A1 | 3/2016 | Flaherty et al. |
| 2016/0074052 A1 | 3/2016 | Keppler et al. |
| 2016/0100907 A1 | 4/2016 | Gomes |
| 2016/0120555 A1 | 5/2016 | Bonin, Jr. et al. |
| 2016/0143744 A1 | 5/2016 | Bojarski et al. |
| 2016/0143749 A1 | 5/2016 | Holovacs et al. |
| 2016/0157937 A1 | 6/2016 | Kehres et al. |
| 2016/0166392 A1 | 6/2016 | Vanasse et al. |
| 2016/0184104 A1 | 6/2016 | Sperling |
| 2016/0193051 A1 | 7/2016 | Budhabhatti et al. |
| 2016/0213385 A1 | 7/2016 | Iannotti et al. |
| 2016/0242933 A1 | 8/2016 | Deransart et al. |
| 2016/0256222 A1 | 9/2016 | Walch |
| 2016/0270854 A1 | 9/2016 | Chaoui et al. |
| 2016/0296285 A1 | 10/2016 | Chaoui et al. |
| 2016/0296290 A1 | 10/2016 | Furrer et al. |
| 2016/0324648 A1 | 11/2016 | Hodorek et al. |
| 2016/0331467 A1 | 11/2016 | Slamin et al. |
| 2016/0345987 A1 | 12/2016 | Guilloux et al. |
| 2016/0361071 A1* | 12/2016 | Mahfouz ............ A61B 17/1739 |
| 2016/0374697 A1 | 12/2016 | Kehres et al. |
| 2017/0000614 A1 | 1/2017 | Mahfouz |
| 2017/0000615 A1 | 1/2017 | Mahfouz |
| 2017/0007330 A1 | 1/2017 | Britton et al. |
| 2017/0027587 A1 | 2/2017 | Fraone et al. |
| 2017/0027593 A1 | 2/2017 | Bojarski et al. |
| 2017/0027702 A1 | 2/2017 | Goldstein et al. |
| 2017/0056024 A1 | 3/2017 | Chao |
| 2017/0056187 A1 | 3/2017 | Humphrey et al. |
| 2017/0079803 A1 | 3/2017 | Lang |
| 2017/0105841 A1 | 4/2017 | Vanasse et al. |
| 2017/0105843 A1 | 4/2017 | Britton et al. |
| 2017/0112626 A1 | 4/2017 | Miller et al. |
| 2017/0119531 A1 | 5/2017 | Bojarski et al. |
| 2017/0150978 A1 | 6/2017 | Iannotti et al. |
| 2017/0151058 A1 | 6/2017 | Sperling |
| 2017/0216038 A1 | 8/2017 | Lang et al. |
| 2017/0231783 A1 | 8/2017 | Lang et al. |
| 2017/0249440 A1 | 8/2017 | Lang et al. |
| 2017/0258598 A1 | 9/2017 | Radermacher et al. |
| 2017/0273795 A1 | 9/2017 | Neichel et al. |
| 2017/0273800 A1 | 9/2017 | Emerick et al. |
| 2017/0273801 A1 | 9/2017 | Hodorek |
| 2017/0281357 A1 | 10/2017 | Taylor et al. |
| 2017/0296347 A1 | 10/2017 | Chua et al. |
| 2017/0304063 A1 | 10/2017 | Hatzidakis et al. |
| 2017/0360567 A1 | 12/2017 | Fitz et al. |
| 2017/0367766 A1 | 12/2017 | Mahfouz |
| 2017/0367828 A1 | 12/2017 | Steines et al. |
| 2017/0367834 A1 | 12/2017 | Fitz et al. |
| 2018/0028325 A1 | 2/2018 | Bojarski et al. |
| 2018/0161176 A1 | 6/2018 | Vivanz et al. |
| 2018/0228614 A1 | 8/2018 | Lang et al. |
| 2018/0235706 A1 | 8/2018 | Asseln et al. |
| 2018/0235762 A1 | 8/2018 | Radermacher et al. |
| 2018/0263782 A1 | 9/2018 | Lang et al. |
| 2019/0015113 A1 | 1/2019 | Morvan |
| 2019/0015116 A1 | 1/2019 | Neichel et al. |
| 2019/0015117 A1 | 1/2019 | Neichel et al. |
| 2019/0015118 A1 | 1/2019 | Neichel et al. |
| 2019/0015119 A1 | 1/2019 | Athwal et al. |
| 2019/0015221 A1 | 1/2019 | Neichel et al. |
| 2019/0038360 A1 | 2/2019 | Chaoui |
| 2019/0175354 A1 | 6/2019 | Knox et al. |
| 2019/0343658 A1 | 11/2019 | Deransart et al. |
| 2020/0188121 A1 | 6/2020 | Boux de Casson et al. |
| 2020/0214845 A1 | 7/2020 | Knox et al. |
| 2020/0289276 A1 | 9/2020 | Lefebvre et al. |
| 2021/0228371 A1 | 7/2021 | Deransart et al. |
| 2021/0228372 A1 | 7/2021 | Knox et al. |
| 2022/0287850 A1 | 9/2022 | Daudet |
| 2022/0354658 A1 | 11/2022 | Knox et al. |

FOREIGN PATENT DOCUMENTS

| | | |
|---|---|---|
| CA | 2938709 | 5/2015 |
| DE | 10 2006 047663 | 4/2008 |
| EP | 1 249 213 | 10/2002 |
| EP | 1 265 555 | 12/2002 |
| EP | 1 563 810 | 8/2005 |
| EP | 1 862 151 | 12/2007 |
| EP | 1 902 689 | 3/2008 |
| EP | 1 952 788 | 8/2008 |
| EP | 2 135 576 | 12/2009 |
| EP | 1 917 051 B1 | 6/2010 |
| EP | 2 243 445 | 10/2010 |
| EP | 2 324 801 A1 | 5/2011 |
| EP | 2 335 655 | 6/2011 |
| EP | 2 501 313 | 9/2012 |
| EP | 2 544 601 | 1/2013 |
| EP | 2583242 | 4/2013 |
| EP | 2 653 136 | 10/2013 |
| EP | 2 845 547 | 3/2015 |
| EP | 2 965 720 | 1/2016 |
| EP | 3057518 | 8/2016 |
| EP | 3057524 | 8/2016 |
| EP | 3065671 | 9/2016 |
| EP | 3068317 | 9/2016 |
| EP | 2 874 570 B1 | 1/2017 |
| EP | 3 117 801 | 1/2017 |
| FR | 2 579 454 | 10/1986 |
| FR | 2 859 099 | 3/2005 |
| FR | 2962573 A1 | 1/2012 |
| FR | 2982694 B1 | 11/2016 |
| FR | 2982979 B1 | 11/2016 |
| FR | 2982693 B1 | 12/2016 |
| GB | 2501494 A | 10/2013 |
| JP | 3179628 U | 11/2012 |
| WO | WO 93/025157 | 12/1993 |
| WO | WO 00/35346 | 6/2000 |
| WO | WO 00/59411 | 10/2000 |
| WO | WO 02/061688 | 8/2002 |

(56) References Cited

FOREIGN PATENT DOCUMENTS

| | | |
|---|---|---|
| WO | WO 2011/110374 | 9/2011 |
| WO | WO 2011/154891 | 12/2011 |
| WO | WO 2011/157961 | 12/2011 |
| WO | WO 2012/021241 | 2/2012 |
| WO | WO 2012/058349 | 5/2012 |
| WO | WO 2013/060851 | 5/2013 |
| WO | WO 2013/062848 | 5/2013 |
| WO | WO 2013/062851 | 5/2013 |
| WO | WO 2013/142998 | 10/2013 |
| WO | WO 2014/035991 | 3/2014 |
| WO | WO 2014/180972 | 11/2014 |
| WO | WO 2015/052586 | 4/2015 |
| WO | WO 2015/056097 | 4/2015 |
| WO | WO 2015/068035 | 5/2015 |
| WO | WO 2015/071757 | 5/2015 |
| WO | WO 2015/175397 | 11/2015 |
| WO | WO 2015/185219 | 12/2015 |
| WO | WO 2017/005514 | 1/2017 |
| WO | WO 2017/007565 | 1/2017 |
| WO | WO 2017/091657 | 6/2017 |
| WO | WO 2017/106294 | 6/2017 |
| WO | WO 2017/184792 | 10/2017 |
| WO | WO 2017/214537 | 12/2017 |
| WO | WO 2018/022227 | 2/2018 |
| WO | WO 2019/014278 | 1/2019 |
| WO | WO 2019/014281 | 1/2019 |
| WO | WO 2019/033037 | 2/2019 |
| WO | WO 2019/060780 | 3/2019 |

OTHER PUBLICATIONS

Non-Final Office Action issued in connection with U.S. Appl. No. 16/904,345, dated Feb. 15, 2022, 35 pages.

Non-Final Office Action issued in connection with U.S. Appl. No. 16/910,663, dated Dec. 15, 2022, 9 pages.

Boileau, et al., "The three-dimensional geometry of the proximal humerus: implications for surgical technique and prosthetic design." The Journal of bone and joint surgery. British vol. 79.5 (1997): 857-865.

Dougherty, "Digital Image Processing for Medical Applications," May 11, 2009 (May 11, 2009), Cambridge University Press, XP002615721.

Favre, et al., "Influence of component positioning on impingement in conventional total shoulder arthroplasty," Clinical Biomechanics, Butterworth Scientifics, Nov. 5, 2007, pp. 174-183, vol. 23, No. 2, Guilford, GB.

Gregory, et al.,"Accuracy of Glenoid Component Placement in Total Shoulder Arthroplasty and Its Effect on Clinical and Radiological Outcome in a Retrospective, Longitudinal, Monocentric Open Study," PLOS One, p. e75791, Aug. 1, 2013, vol. 8, No. 10.

Habets, et al., Computer assistance in orthopaedic surgery. Technische Universiteit Eindhoven, 2002.

Hempfing, et al. "Surgical landmarks to determine humeral head retrotorsion for hemiarthroplasty in fractures." Journal of shoulder and elbow surgery 10.5 (2001): 460-463.

Hernigou, et al., "Determining humeral retroversion with computed tomography." Journal of bone and joint surgery. Oct. 2002;84-A(10):1753-62.

Iannotti et al., "Prosthetic positioning in total shoulder arthroplasty," Journal of Shoulder and Elbow Surgery, Jan. 1, 2005, vol. 14, No. 1S, pp. S111-S121.

Kobashi et al., "Knowledge-Based Organ Identification from CT Images," Pattern Recognition, Elsevier, GB, vol. 28, No. 4, Apr. 1, 1995 (Apr. 1, 1995), pp. 475-491, XP004013165.

Lee, C.C. et al., "Identifying multiple abdominal organs from CT image series using a multimodule contextual neural network and spatial fuzzy rules", IEEE Transactions on Information Technology in Biomedicine, IEEE Services Center, Los Alamitos, CA, US, vol. 7, No. 3, Sep. 1, 2003 (Sep. 1, 2003) pp. 208-217, XP011100536.

Lee, C.C. et al., "Recognizing Abdominal Organs in CT Images Using Contextual Neural Network and Fuzzy Rules", Engineering in Medicine and Biology Society, 2000. Proceedings of the 22nd Annual International Conference of the IEEE Jul. 23-28, 2000, Piscataway, NJ, USA, IEEE, vol. 3, Jul. 23, 2000 (Jul. 23, 2000), pp. 1745-1748, XP010530837.

Ma, et al., "Robust registration for computer-integrated orthopedic surgery: laboratory validation and clinical experience." Medical image analysis 7.3 (2003): 237-250.

"Olympia Total Shoulder Surgical Technique", Wright Medical Technology, 2001, in 19 pages.

Nguyen, et al., "A New Segmentation Method for MRI Images of the Shoulder Joint", Computer and Robot Vision, 2007. CRV '07. Fourth Canadian Conference on, IEEE, PI, May 1, 2007 (May 1, 2007), pp. 329-338, XP031175821.

Radermacher, K., et al., "Computer Assisted Orthopaedic Surgery with Image Based Individual Templates," Clinical Orthopaedics and Related Research, No. 354, Sep. 1998, pp. 28-38.

Radermacher, K., et al., "Image Guided Orthopedic Surgery Using Individual Templates: Experimental Results and Aspects of the Development of a Demonstrator for Pelvis Surgery", Health Care Sector, Telematics Applications Program, 1997, pp. 606-615.

Tamez-Pena et al., "The Integration of Automatic Segmentation and Motion Tracking for 4D Reconstruction and Visualization of Musculoskeletal Structures," Biomedical Image Analysis, 1998. Proceedings. Workshop on Santa Barbara, CA US, Jun. 26-27, 1998, Los Alamitos, CA, USA, IEEE Comput. Soc. US, Jun. 26, 1998 (Jun. 26, 1998), pp. 154-163, XP010291418.

Valstar, et al. "Towards computer-assisted surgery in shoulder joint replacement." ISPRS journal of photogrammetry and remote sensing 56.5-6 (2002): 326-337.

Valstar, et al. "The use of Roentgen stereophotogrammetry to study micromotion of orthopaedic implants." ISPRS journal of photogrammetry and remote sensing 56.5-6 (2002): 376-389.

Welsh, et al., "CT-based preoperative analysis of scapula morphology and glenohumeral joint geometry." Computer Aided Surgery 8.5 (2003): 264-268.

Wu, et al. "An interface for the data exchange between CAS and CAD/CAM systems." International Congress Series. vol. 1256. Elsevier, 2003.

Zimmer, "Zimmer® PSI Shoulder Trabecular MetalTM Reverse Glenoid Base Plate Surgical Technique", Dec. 30, 2013.

"Zimmer® PSI Shoulder Planning", Zimmer Biomet TV, posted Jul. 11, 2014, retrieved from internet on Jan. 9, 2020, https://zimmerbiomet.tv/videos/1025?a=surgeon&version=1190>.

First Office Action issued in corresponding Japanese Patent Application No. 2021-506973, dated Jun. 5, 2023, 5 pages.

First Examination Report issued in connection with corresponding Australian Patent Application No. 2016371425, dated Nov. 11, 2020, 5 pages.

Communication Pursuant to Article 94(3) issued in connection with European Patent Application No. 18746503.4, dated Oct. 17, 2023, 5 pages.

Non-Final Office Action issued in connection with U.S. Appl. No. 17/650,722, dated Nov. 15, 2023, 10 pages.

Notice of Allowance issued in connection with U.S. Appl. No. 17/645,607, dated Dec. 20, 2023, 11 pages.

* cited by examiner

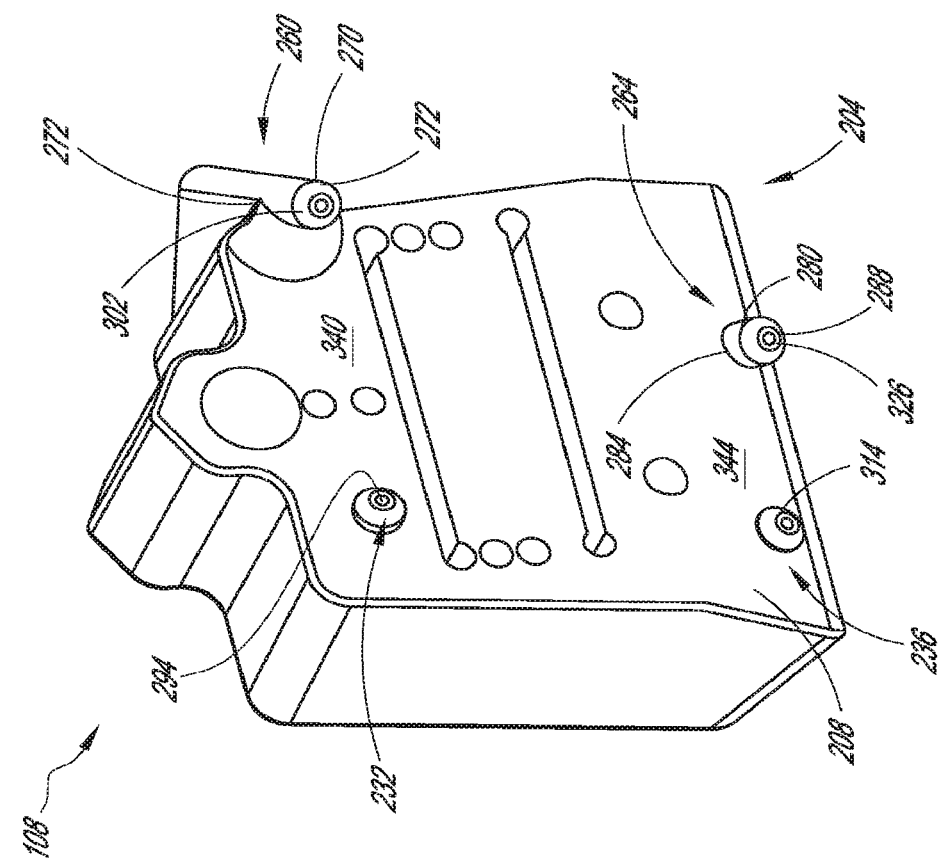

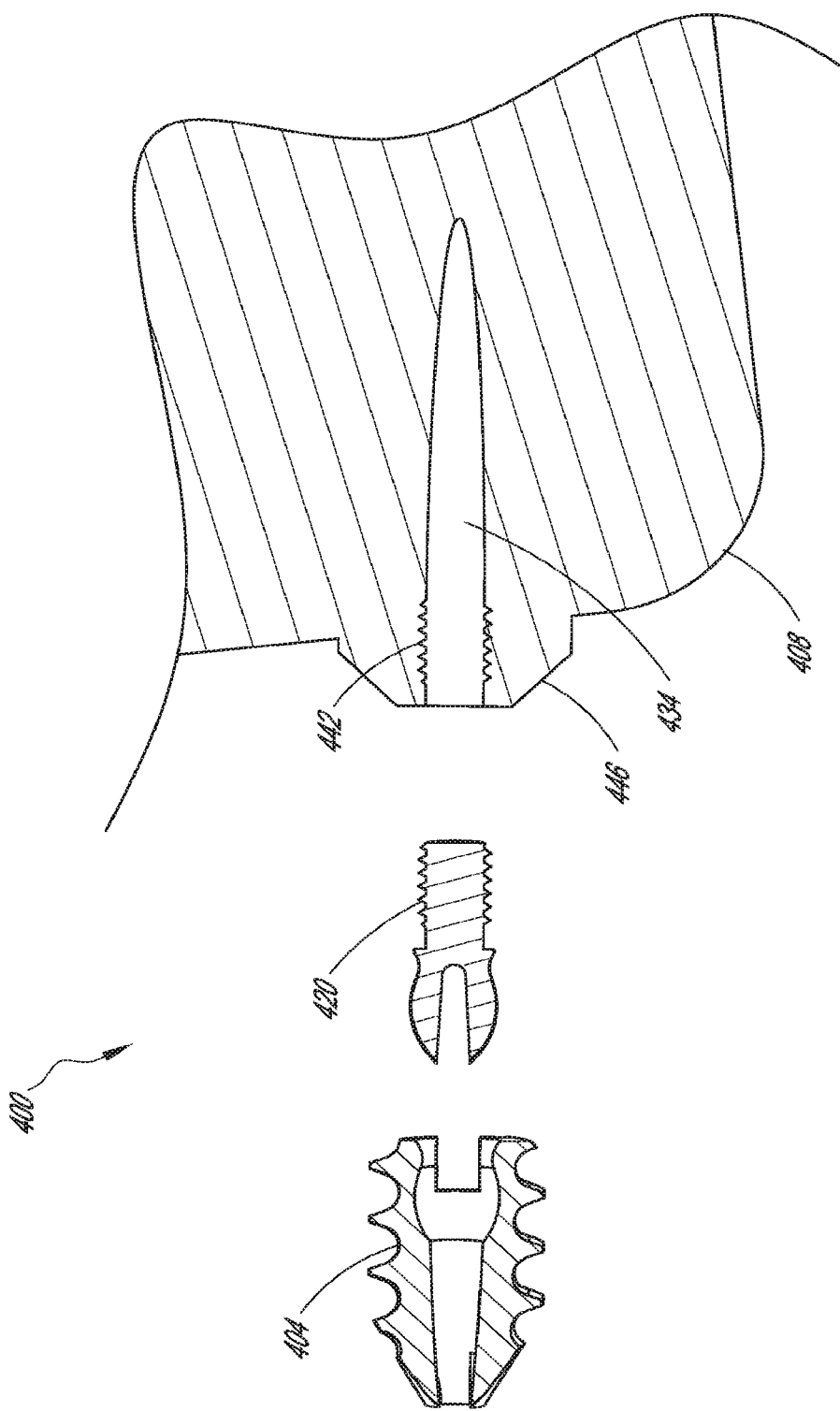

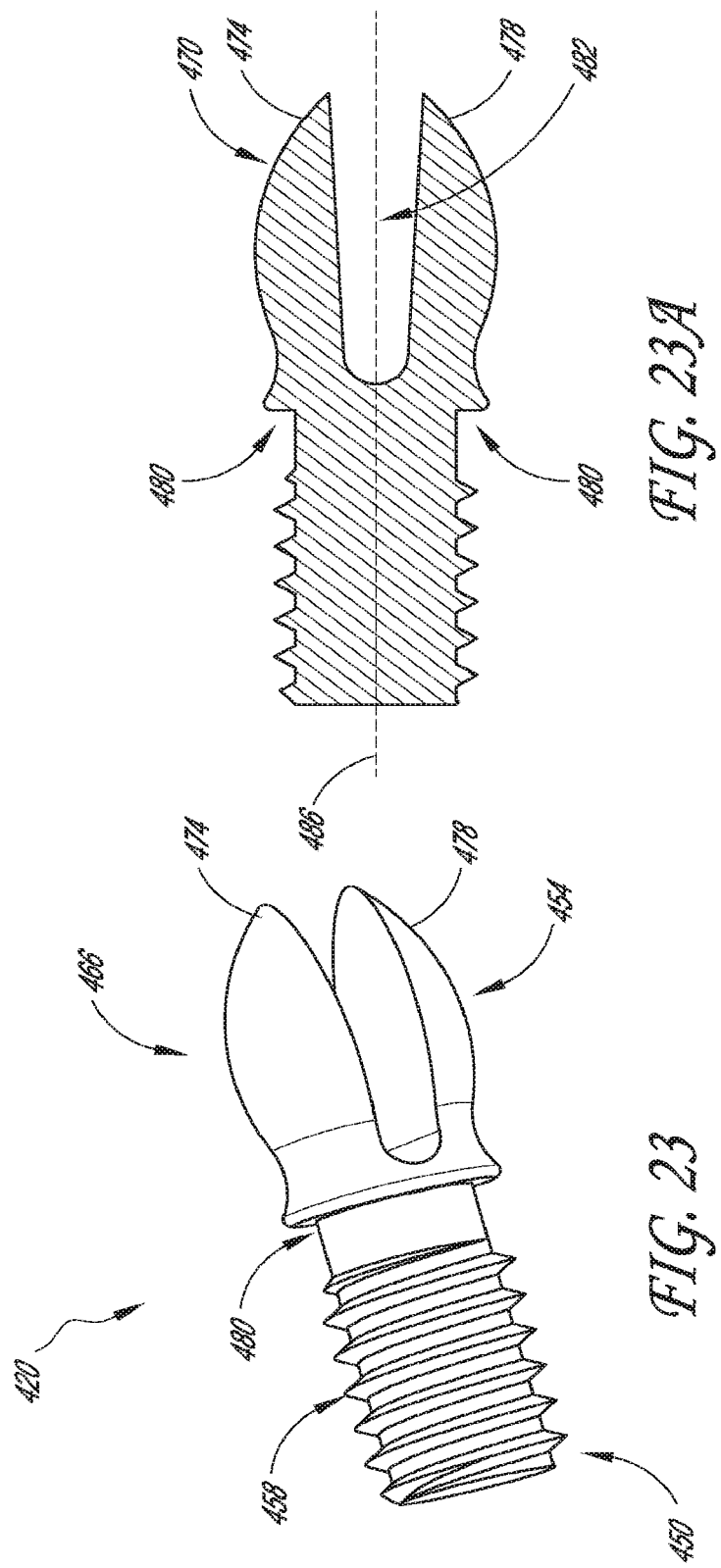

PATIENT SPECIFIC INSTRUMENTS AND METHODS FOR JOINT PROSTHESIS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 C.F.R. § 1.57.

BACKGROUND OF THE INVENTION

Field of the Invention

This application is directed to methods and apparatuses used to install a joint prosthesis using patient specific instruments.

Description of the Related Art

Patient specific instruments (PSI) refer to specially manufactured instruments that incorporate the patient's own bone geometry data. The instruments can be accurately positioned because they are formed with reference to the patient's bone data and when formed in this manner have features that engage selected landmarks on the bone to assure proper positioning. An imaging technology, such as computerized tomography (CT) scanning, is used to acquire the bone data prior to surgery. Three dimensional (3D) models of bone are used to align a 3D model of a prosthesis. These models are provided to a system that constructs the patient specific instruments such that when applied to the bone the patient specific instruments produce the bone cuts needed for installing the prosthesis accurately.

One advantage of patient specific instruments is that they may include planning software that allows a surgeon or technician to manipulate the 3D models of the bones. Here the surgeon or technician can correct deformities in the relationship of the bones, e.g., the relationship of the talus to the tibia. These deformities can include one or more of varus/valgus alignment, anterior/posterior or medial/lateral subluxation, subsidence and/or distractions. Once the bones are aligned properly, the surgeon may select the appropriate size prosthesis and align it to and place it in its desired position. The position of the bones to the prosthesis in the absence of deformity is an input to the design of the patient specific instruments in order to make accurate cuts in the bone.

Thus, deformities can be corrected with the help of the patient specific instruments in surgery.

SUMMARY OF THE INVENTION

While patient specific instruments can be formed with reference to bony landmarks as discussed above, this approach is in need of improvement. Bony landmarks are disposed under soft tissue and vary from patient to patient in location and size. This variation introduces complexity in exposing and consistently locating a landmark to be used as a registration point. While landmarks can be exposed by dissecting the soft tissue, dissection is time consuming, not always effective, and is invasive. It would be faster and less invasive to place an instrument that includes a patient specific component, without dissecting away the soft tissue. Further, patient specific guides placed against soft tissue may compress the soft tissue and the location of the guide can vary when placed against soft tissue. Therefore, it would be an advance to provide methods and structures that can provide a consistent, easy to access registration structure across a wide range of patients.

Methods herein to form a patient specific instrument can include three parts or phases: (1) installing reference bushing(s) and gathering 3D spatial location information including the location of the bushings; (b) designing and manufacturing patient specific cutting guides based on the spatial location information (e.g., based on the 3D data) of reference bushing, bone geometry and desired implant location; and (c) performing surgery using reference bushing(s) and patient specific cutting guides.

In an example method, one or more reference bushings are advanced into a tibia adjacent to an ankle joint of a patient. One or more reference bushings are advanced into a talus adjacent to the ankle joint. After the reference bushings are advanced into the tibia and talus, information of the spatial location of the reference bushings and a portion of the tibia and talus around the reference bushings is obtained. The spatial location information can include imaging and/or three-dimensional spatial location information. From the information (e.g., the 3D data), cutting guides are designed taking into account the specific location of the reference bushings, the specific bone geometries, and the proposed location of joint replacement implant. Patient specific cutting guides are manufactured in preparation for joint replacement surgery. Thereafter, in surgery, a patient specific cutting guide is connected to the reference bushings. First, second, and/or more reference bushings are located on, and can be connected to, the patient specific cutting guide based upon the spatial location information. When the patient specific cutting guide is coupled to the patient, a gap is provided between the patient specific guide and at least one of the tibia and the talus.

In one embodiment, a surgical method is provided. A first reference bushing is advanced into a tibia adjacent to an ankle joint of a patient. A second reference bushing is advanced into a talus adjacent to the ankle joint. Three dimensional spatial location information is obtained after the first reference bushing is advanced into the tibia and after the second reference bushing into the talus. The three dimensional spatial location information is of the first reference bushings and a portion of the first reference bushing around the tibia and is of the second reference bushing and a portion of the talus around the second reference bushing. A patient specific cutting guide is connected to the first reference bushings and to the second reference bushing in surgery. The first and second reference bushings are connected to the patient specific cutting guide at locations of the patient specific cutting guide based upon the three dimensional spatial location information. When the patient specific cutting guide is coupled to the patient, a gap is provided between the patient specific guide and at least one of the tibia and the talus.

In another surgical method according to this application, a first bone reference is provided on or in a first bone surface adjacent to a joint of a patient. A second bone reference is provided on or in a second bone surface adjacent to the joint of the patient. A first reference feature of a patient specific cutting guide is coupled with the first bone reference after providing the first bone reference. A second reference feature of the patient specific cutting guide is coupled with the second bone reference after providing the second bone reference. The steps of coupling can be performed without disrupting soft tissue or bone adjacent to the joint.

Examples are provided herein of using this method for ankle surgery. An advantage for ankle surgery is that these methods reduce or eliminate the need for dissections and other soft or hard tissue disruption in connection with an ankle surgery. These advantages are also applicable to other joints. For instance, a joint surgery involving placement of an implant on each side of a joint can benefit from reducing the need to clear soft tissues from the adjacent bone portions. Such advantages can be directly applied to a wrist, an elbow or a knee. For instance a bone reference, such as a reference bushing can be placed in one or more of a distal radius, a distal ulna, a proximal portion of a scaphoid, lunate, triquetrum and/or other bone of the hand. A bone reference, such as a reference bushing can be placed in one or more of a distal portion of a humerus, a proximal portion of a radius, and/or a proximal portion of an ulna. A bone reference, such as a reference bushing can be placed in one or more of a distal portion of a femur, a proximal portion of a tibia, and/or a proximal portion of a fibula. Once so placed, a patient specific guide can be formed based on positional information and surgery on these joints can be completed without disruption or with reduced disruption of soft and hard tissues.

In another embodiment, a method of manufacturing a patient specific guide is provided. Spatial location information is received. The spatial location information includes a position of at least two reference bushings disposed in at least two bone locations. The spatial location information includes the location and/or the form of the at least two bone locations. Based upon the spatial location information, a patient specific guide is manufactured. The patient specific guide is configured to position at least one cutting feature relative to at least one of the bone locations. In the method, a first reference member is formed to mate with the first reference bushing. A second reference member is formed to mate with the second reference bushing. The first and second reference members have a length sufficient to create clearance from the bone when the first and second reference members are so mated.

In another embodiment, a joint prosthesis bone preparation system is provided. The joint prosthesis bone preparation system can be for an ankle procedure in some embodiments. The system includes a first reference bushing, a second reference bushing and a patient specific cutting guide. The first reference bushing has a distal portion configured to be advanced into a first portion of an anatomical joint. The second reference bushing has a distal portion configured to be advanced into a second portion of the anatomical joint. The patient specific cutting guide has an anterior surface, a posterior surface and at least one cutting feature. The cutting feature extends from the anterior surface to the posterior surface. The posterior surface has a first reference feature configured to contact the first reference bushing. The posterior surface has a second reference feature configured to contact the second reference bushing. The system is configured such that when the patient specific cutting guide is coupled with the first and second reference bushings a clearance gap is provided between the posterior surface and the first portion of the anatomical joint and/or between the posterior surface and the second portion of the anatomical joint.

In another embodiment a joint prosthesis bone preparation system is provided that includes a first reference bushing, a second reference bushing and a patient specific cutting guide. The joint prosthesis bone preparation system can be for an ankle procedure in some embodiments. The first reference bushing has a distal portion configured to be advanced into a first portion of a joint. The second reference bushing has a distal portion configured to be advanced into a second portion of a joint. The patient specific cutting guide has an anterior surface, a posterior surface, and at least one cutting feature extending from the anterior surface to the posterior surface. The posterior surface has a first reference feature configured to contact the first reference bushing. The first reference bushing includes a surface configured to limit movement of the patient specific cutting guide. The posterior surface has a second reference feature configured to contact the second reference bushing. The second reference bushing includes a surface configured to limit movement of the patient specific cutting guide. The first and second reference features are disposed at spaced apart locations. The posterior surface is disposed at a location such that when the patient specific cutting guide is coupled with the first and second reference bushings a clearance gap is provided between the posterior surface and the first portion of the joint and/or between the posterior surface and the second portion of the joint.

In another embodiment, a system for preparing an ankle bone to receive an ankle prosthesis is provided. The system includes a patient specific cutting guide that has an anterior surface, a posterior surface, and at least one cutting feature extending through the guide from the anterior surface. The posterior surface comprising a first protrusion or other member that extends from a first end fixed to the posterior surface to a second end disposed away from the first end of the first protrusion. The posterior surface has a second protrusion or other member that extends from a first end fixed to the posterior surface to a second end disposed away from the first end of the second protrusion. The first and second protrusions are spaced apart and have a length such that when the patient specific cutting guide is coupled with first and second bone references a clearance gap is provided between the posterior surface and the ankle bone.

In another embodiment, a patient specific surgery cutting guide is provided. The patient specific surgery cutting guide includes a first surface, a second surface opposite the first surface, and at least one cutting feature extending from the first surface to the second surface. The second surface has a first bone interface portion, e.g., a first bone reference, and a second bone interface portion, e.g., a second bone reference. At least one of the first bone interface portion and the second bone interface portion has a mating reference feature to provide isolated, e.g., discrete, contact with a bone reference. When the patient specific surgery cutting guide is applied to the patient such that the mating reference feature is in contact with the bone reference, a clearance gap is provided between bone and regions of the second surface adjacent to the mating reference feature. Advantageously, the bone reference can be a reference bushing. In various methods, the reference bushing can be applied to only one bone and need not be applied in the vicinity of a joint. Reference bushings can be applied to more than one bone and need not be applied in the vicinity of the joint. Then a cutting or other guide can be located on the reference bushings and a procedure on the bone carried out.

Any of the systems herein can include a device for determining three dimensional location information of bones or other dense objects, such as CT scanners. Any of the systems herein can include rapid production devices, such as 3D printers to form patient specific components.

In various methods, one or more reference bushing is inserted prior to CT scanning or other imaging technique and surgery. The method can happen in two phases. First the bushings can be placed, in some embodiments percutaneously. Later, e.g., an hour or several hours, a day or several days to several weeks later, the location information can be obtained. Subsequently, e.g., an hour or several hours, a day or several days to several weeks later, a surgery can be performed using the reference bushings. In the surgery, the bushing(s) are accurate registration points for attaching the cutting guide in the methods described herein. This alleviates the need to designate and find bone surface landmarks, which are often covered with soft tissues, and are difficult to expose. Therefore reference bushing(s) are more accurate than traditional bony landmarks.

BRIEF DESCRIPTION OF THE DRAWINGS

These and other features, aspects and advantages are described below with reference to the drawings, which are intended to illustrate but not to limit the inventions. In the drawings, like reference characters denote corresponding features consistently throughout similar embodiments. The following is a brief description of each of the drawings.

FIG. 4 is a perspective view of an anterior portion of a cutting guide that has patient specific attributes;

FIG. 5 is a perspective view of a posterior portion of the cutting guide of FIG. 4;

FIG. 21 is a cross-sectional view of a bone preparation system.

FIG. 23-23A show a variation of a reference bushing configured to receive and couple with a bone preparation guide by way of a snap fit configuration.

DETAILED DESCRIPTION OF THE PREFERRED EMBODIMENT

This application is directed to patient specific instruments, such as cutting guides, tools, and methods that can be used in joint procedures. The tools can be used to place an ankle prosthesis, a shoulder or other prosthesis and, in some cases, correct deformity in a joint. As discussed in greater detail below the apparatuses and methods herein enable the bones around a joint to be prepared with minimal incisions and relatively little to no soft tissue scraping. While small incisions may be formed for cutting bones and introducing prosthesis components, the apparatuses and methods herein allow a surgeon to avoid excessive incisions and excessive tissue removal around the bone. For instance these apparatuses and methods can enable a surgeon to not disturb or minimally disturb the periosteum, which is a dense connective tissue attached to the bone which in prior art methods is required to be mostly or completely scraped off the bone.

Figure 1B:
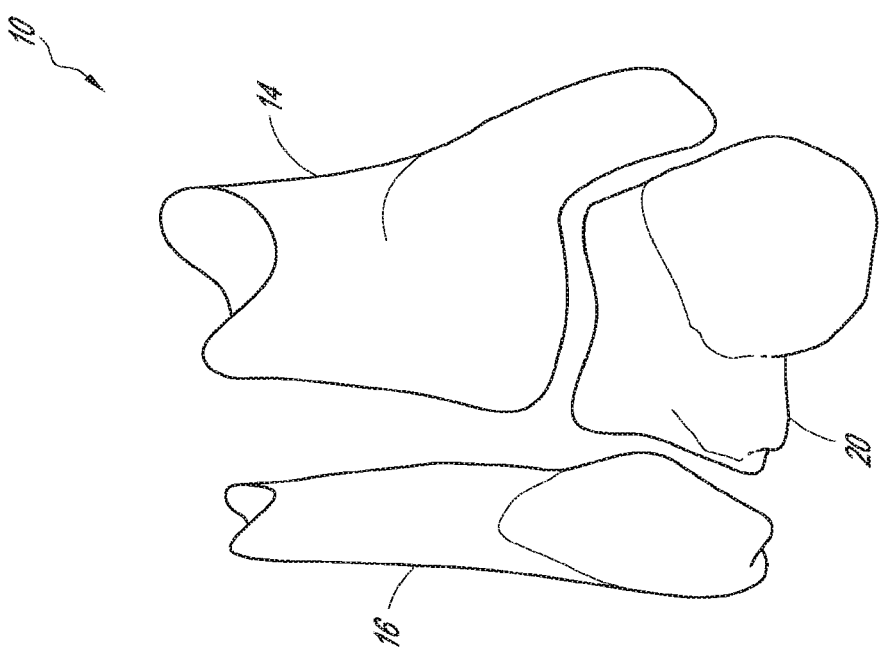
FIG. 1B is a schematic diagram showing a reduction or elimination of the deformity of FIG. 1A, which can be accomplished using the instruments disclosed herein.
Figure 1A:
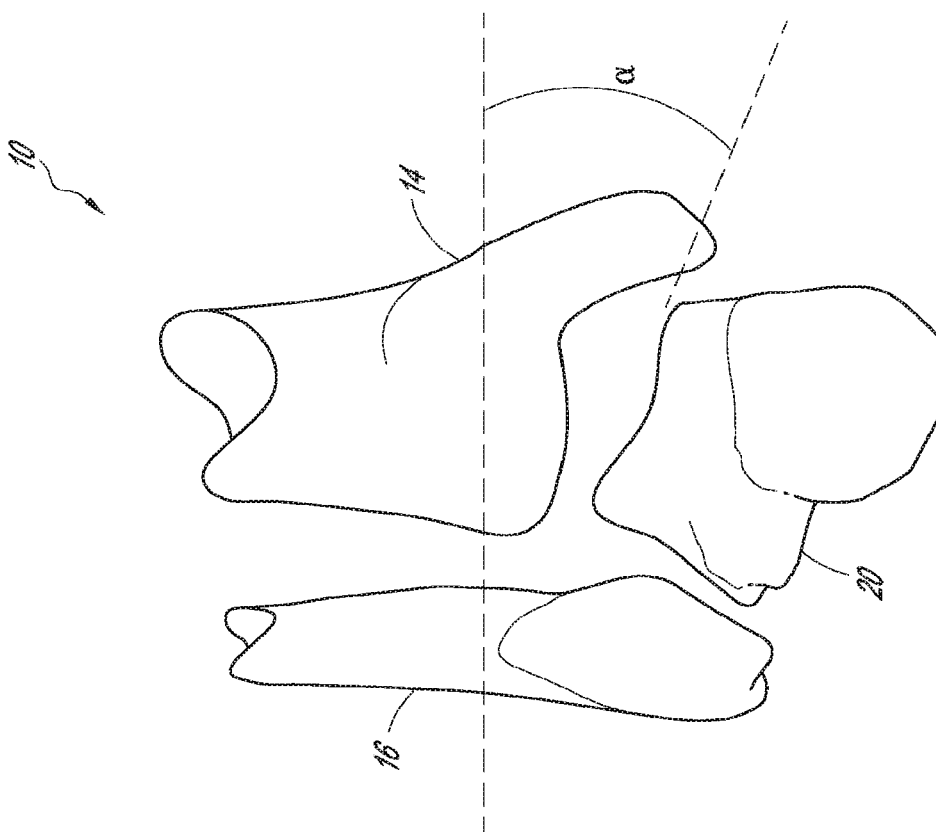
FIG. 1A is a schematic diagram showing an example of ankle deformity that can be corrected using patient specific instrumentation described and claimed herein.

FIG. 1A shows an ankle joint 10 in a state of deformity and FIG. 1B shows a state in which the deformity is reduced or is not present. The ankle joint 10 is formed between a tibia 14, a fibula 18, and a talus 20. The state of deformity illustrated is known as varus/valgus misalignment, which a plane tangential to the superior surfaced of the talus 20 is at an angle α to a horizontal plane. Other forms of deformity include one or more of medial/lateral subluxation, anterior/posterior subluxation, subsidence and distraction. The misalignment of any deformity creates discomfort and degradation of the joint. While the joint could be replaced without correcting the deformity such a replacement joint would not function properly, potentially causing pain and premature failure of the replacement joint. For this patient correcting the deformity at the same time as replacing the ankle joint will make for a more effective treatment.

Figure 2:
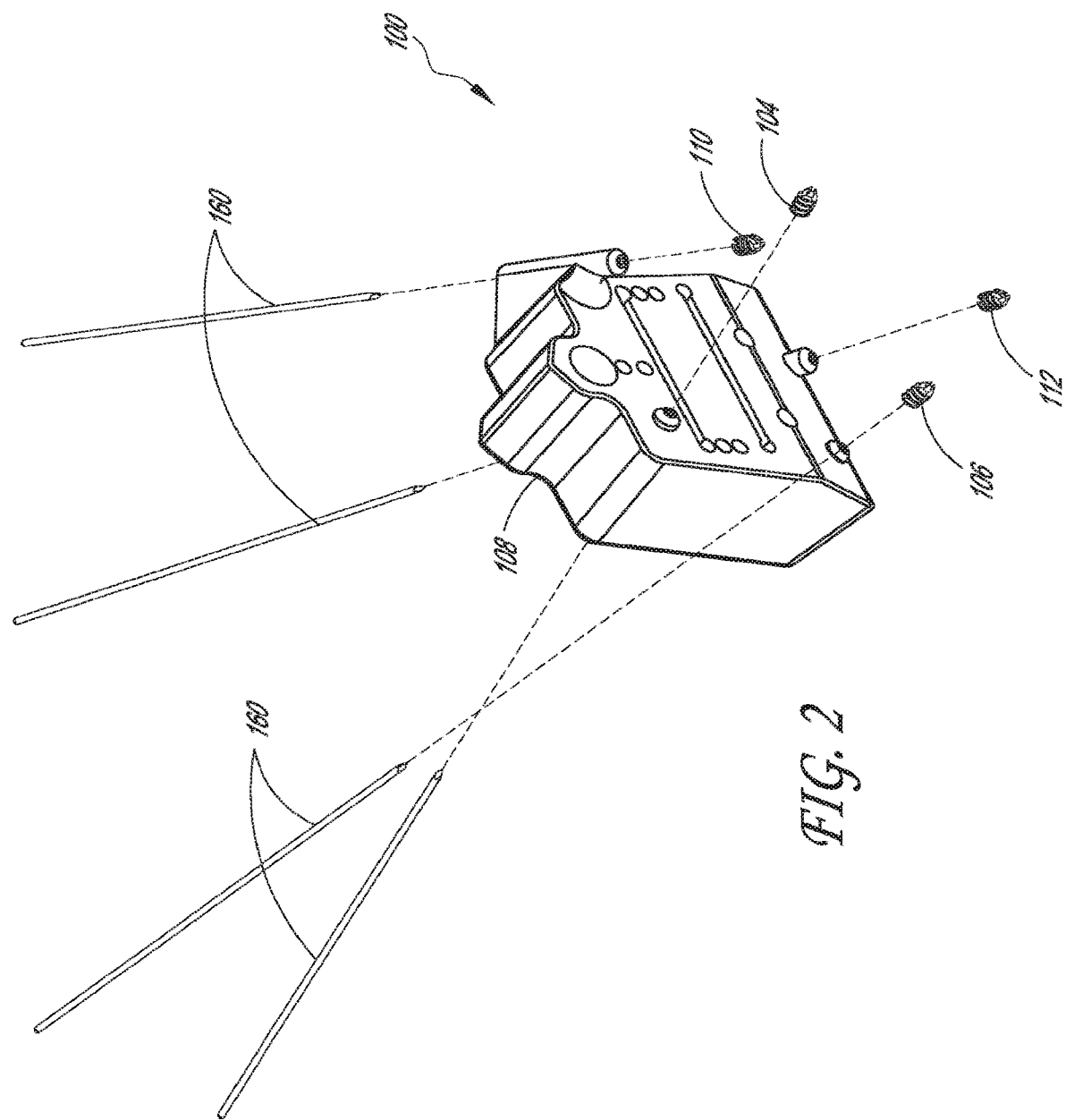
FIG. 2 shows an ankle prosthesis bone preparation system that includes a plurality of bone reference bushings and a patient specific cutting guide for an ankle procedure.

FIG. 2 shows a bone preparation system 100, which is adapted for preparing an ankle to receive an ankle prosthesis. The bone preparation system 100 includes a first reference bushing 104, a second reference bushing 106, and a cutting guide 108. The first reference bushing 104 and the second reference bushing 106 are examples of bone references. As discussed further below, other bone references can include naturally present bony prominences, channels or openings formed in the bone or other landmarks. The bone preparation system 100 also can include a third reference bushing 110 and a fourth reference bushing 112. The first and third reference bushings 104, 110 can be placed in a first bone portion to a joint, e.g., in the tibia as shown in FIG. 7.

Figure 7:
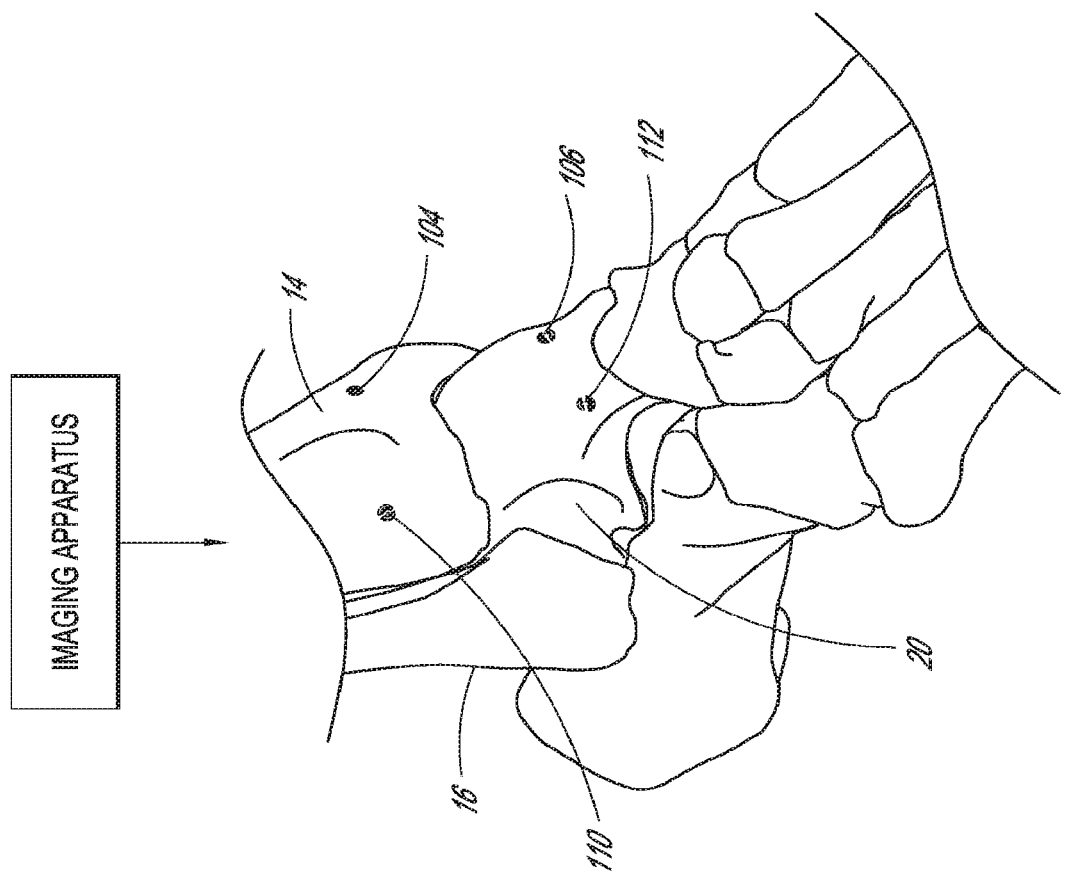
FIG. 7 illustrates another portion of a method in which spatial location information in three-dimensions is acquired for a specific patient.

The second and fourth reference bushings 106, 112 can be placed in a second bone portion adjacent to the joint, e.g., in the talus as shown in FIG. 7. In one method using the ankle surgery system 100, the first reference bushing 104 can be placed in a medial, distal and anterior aspect of the tibia 14 and the third reference bushing 110 can be placed on a lateral, distal, and anterior aspect of the tibia 14. The second reference bushing 106 can be placed in a medial portion of the neck of the talus 20 and the fourth reference bushing 112 can be placed in a lateral portion of the neck of the talus 20.

Figure 3A:
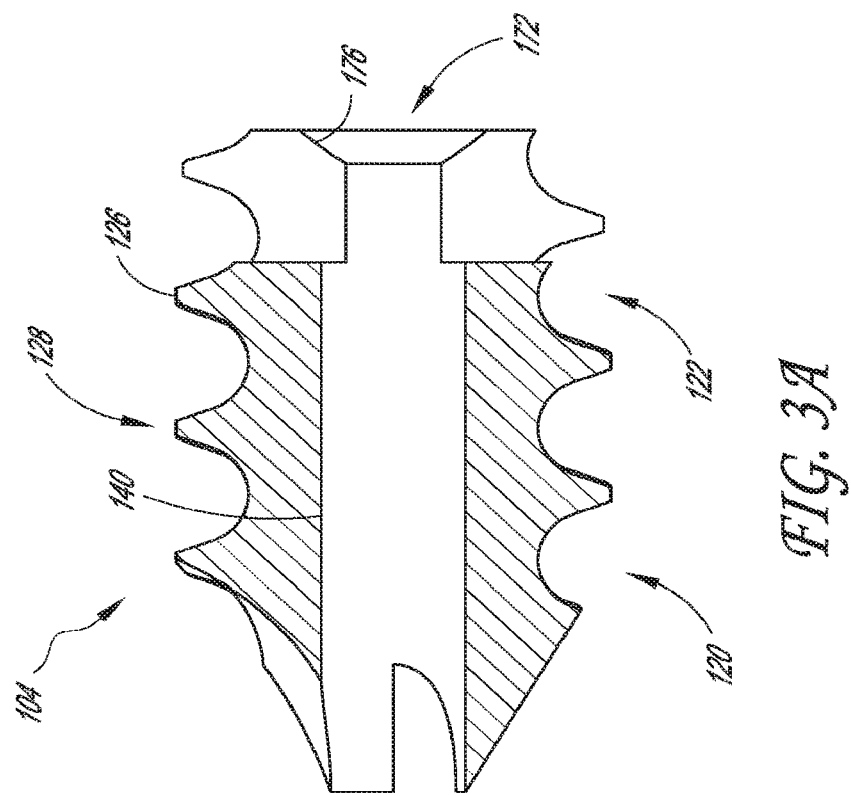
FIG. 3A shows a cross-sectional view of the reference bushing of FIG. 3, taken along section plane 3A-3A.
Figure 3:
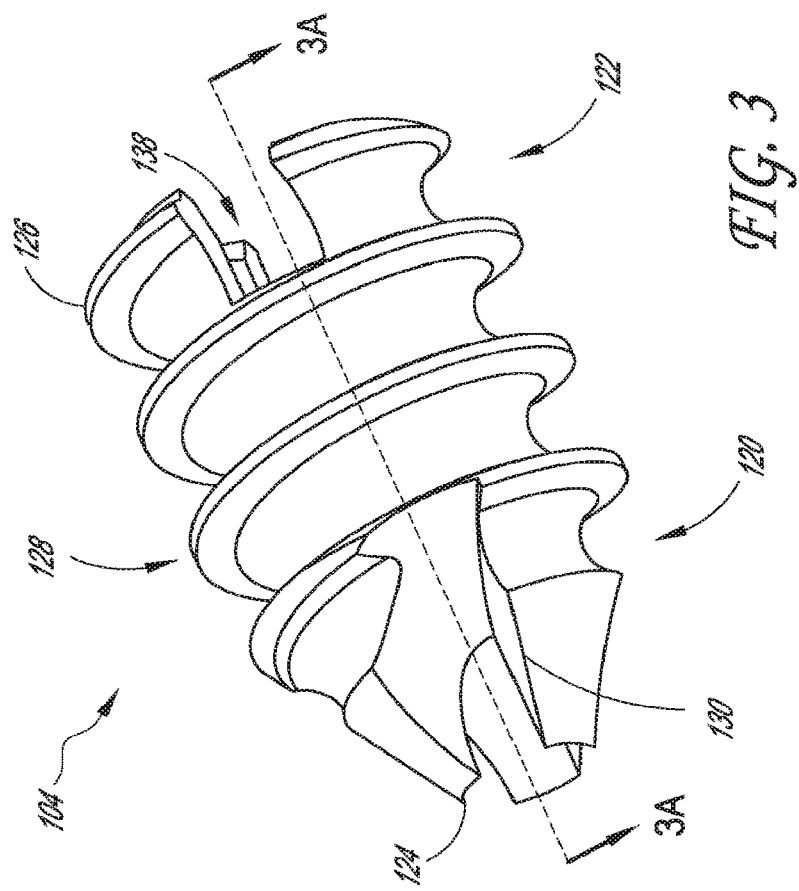
FIG. 3 is a perspective view of a reference bushing, which can be used as a bone reference in various methods disclosed and claimed herein.

FIG. 3 shows one embodiment of the reference bushing 104. The reference bushing 104 has a distal portion 120 and a proximal portion 122. The distal portion 120 extends proximally from a distal end 124 of the bushing 104. The proximal portion 122 extends distally from a proximal end 126 of the bushing 104. The distal portion 120 is adapted to be advanced into bone. The distal portion 120 can have threads 128 to allow the bushing 104 to be threaded into the bone. In other embodiments, the distal portion 120 is configured to be advanced into the bone and to engage the bone by interference fit. These and other means for engaging an implant with bone can be used in any of the reference bushings described herein. The distal portion 120 can include milling features 130, including sharp edges, barbs or flutes to ease insertion of the reference bushing 104 into the bone. In another embodiment, the distal portion 120 is not threaded. The distal portion 120 can have a flat, tapered, or other configuration suitable for direct axial advancement into the bone rather than rotation as with the reference bushing 104.

FIGS. 3 and 3A show a tool interface 138 at the proximal end 126 of the reference bushing 104. The tool interface 138 enables the bushing 104 to be advanced into the bone, e.g., following the threads 128. In the illustrated embodiment, the threads 128 extend from the proximal end 126 to the distal end 124 of the first bushing 104. By providing the threads 128 over the entire length of the bushing 104, the bushing can be advanced entirely into the bone surface to be flush with the bone when so advanced.

FIGS. 3 and 3A show that the reference bushing 104 can be cannulated, having a lumen 140 that extends from a proximal end 144 to a distal end 148 of the bushing 104. The lumen 140 can be configured to allow the reference bushing 104 to be advanced over a wire into the bone or to receive a fixation pin. FIG. 2 shows that the bone preparation system 100 can include a fixation pin 160 to be advanced through the lumen 140. To provide secure fixation in a desired orientation relative to the talus 20 or other bone portion two or more fixation pins 160 can be provided for securing the cutting guide 108 to the talus 20. To provide secure fixation in a desired orientation relative to the tibia 14 or other bone portion two or more fixation pins 160 can be provided for securing the cutting guide 108 to the tibia 14, e.g., through the first and third reference bushings 104, 110. In other embodiments, any of the reference bushings 104, 106, 110, 112 may have an internal thread rather than the smooth lumen, for attachment to a patient specific cutting guide using a mating screw rather than a pin. The screw can be a separate component in some embodiments. In other embodiments, an external surface of one or more of the reference features discussed below can be threaded and the reference features can be rotatable relative to the body of the cutting guide 108 such that the reference features can serve both a locating and a securing function. In some systems, some of the references bushings 104, 106, 110, 112 have lumens that are at least partially threaded and other of the references bushings 104, 106, 110, 112 can have smooth lumens without threads.

The first reference bushing 104 includes a motion limiting portion 172 configured for holding the patient specific cutting guide 108 at a selected position and/or orientation relative to the tibia 14 (or other first bone portion). The motion limiting portion 172 can include a concave surface 176. The concave surface 176 is configured to receive a portion of the cutting guide 108 to hold the cutting guide relative to the ankle (or other) joint. The concave surface 176 can be rounded, e.g., spherical, to facilitate rotating or otherwise positioning the cutting guide 108 to align apertures therein with the lumen 140 of the bushing 104.

In the illustrated embodiment, each of the first reference bushing 104, the second reference bushing 106, the third reference bushing 110, and the fourth reference bushing 112 can have a concave surface 176 to receive a portion of and limit the motion of the cutting guide 108.

FIGS. 4 and 5 illustrate one embodiment of the cutting guide 108 that is suited for preparing bones around the ankle joint 10 to receive an ankle prosthesis. The cutting guide 108 is merely illustrative. Other cutting guides may be configured to engage reference bushings. Accordingly, cutting guides usable in the systems and methods claimed herein are not limited to those shown and described herein. The cutting guide 108 can be custom made for a specific patient, as discussed further below.

The cutting guide 108 includes a first side 200 that includes a first surface 202 and a second side 204 opposite the first side 200. The second side 204 includes a second surface 208. The first side 200 of the cutting guide 108 is an anterior surface of the cutting guide when the cutting guide is used for preparing an ankle joint. The second side 204 is a posterior surface of the cutting guide 108 in an ankle joint application.

The cutting guide 112 includes at least one cutting feature 216 that extends therethrough from the first surface 200 to the second surface 204. The cutting feature 216 includes a planar medial-lateral surface in the illustrated embodiment. A surface 203 at the bottom of the cutting guide 108 as illustrated in FIG. 4 is a distal surface. A surface 205 at a top of the cutting guide 108 as illustrated in FIG. 4 is a proximal surface. The cutting guide 108 can include two cutting features 216 with parallel planar medial-lateral cutting surfaces. Where two cutting features 216 are provided, a first surface 216 can be disposed closer to the surface 205 than to the surface 203 while a second cutting surface 216 can be positioned between first cutting surface and the surface 203. The cutting guide also can include distal-proximal cutting features 218. The cutting features 218 are illustrated as an array of spaced apart openings, but could include slots or other features providing guided access to a cutting device through the cutting block 108. In alternate embodiments, cutting features need not be parallel to one another and can be disposed at various angles with respect to one another and be disposed at various locations within the cutting block, depending on the type of implant used.

The second side 204 has a first reference feature 232 and a second reference feature 236. The first reference feature 232 is configured to contact the first reference bushing 104. In certain embodiments as discussed further below, the contact between the reference feature 232 and the bushing 104 can include or be augmented by placing a pin through lumens in the reference feature 232 and the bushing 104. In other embodiments, the contact between the reference feature 232 and the bushing 104 can include or be augmented by a snap-fit connection between the reference feature 232 and the bushing 104. For example, the proximal portion 122 could be configured to expand slightly to permit a portion of the reference feature 232 that is larger than the unexpanded size of the proximal portion 122 to be inserted into the proximal portion 122. In other embodiments, the proximal portion 122 of can be configured to be received in the reference feature 232 and when so received to cause expansion of the reference feature such that a snap-fit connection is formed. Further aspects of snap-fit connections are discussed below in connection with FIGS. 20-23A. In other embodiments, a screw connection is provided between one or more reference feature and bushing. The second reference feature 236 is configured to contact the second reference bushing 108. When the first and second reference features 232, 236 contact the first and second reference bushings 104, 108 the reference bushings limit the movement of the cutting guide 108 relative to the bone or bones or the joint. FIG. 5 shows that the first and second reference features 232, 236 can be disposed at spaced apart locations on the second side 204 of the cutting guide 108.

The first and second reference features 232, 236 are configured such that when the patient specific cutting guide is coupled with the first and second reference bushings 104, 106 a clearance gap G (see FIG. 2) is provided between the second surface 208 and the bone or the joint beneath the cutting guide 108. The gap G can space a portion or all of the second surface 208, which is on the second side 204 of the cutting guide 108 facing the bone or bones, from the bone or bones around the joint being prepared for a prosthesis. For example, a posterior surface of the cutting guide 108 that extends from the first reference feature 232 to the second reference feature 236 does not contact the tibia or the talus 20 between the first reference bushing 104 and the second reference bushing 106, as shown in FIG. 2. In one embodiment, the cutting guide 108 is configured such that when the cutting guide 108 contacts the first and second reference bushings 104, 106 the cutting guide 108 is spaced apart from and does not contact the tibia 14. In one embodiment, the cutting guide 108 is configured such that when the cutting guide 108 contacts the first and second reference bushings 104, 106 the cutting guide 108 is spaced apart from and does not contact the talus 20. In one embodiment, the cutting guide 108 is configured such that when the cutting guide contacts the first and second reference bushings 104, 106 the cutting guide 108 only contacts a plurality of reference bushings, e.g., any combination of two or more of the reference bushings 104, 106, 110, 112 and does not contact the tibia or the talus. The gap G provides sufficient clearance to allow irregular prominences of the bone and/or underlying soft tissues to be accommodated in the space under the cutting guide 108 without requiring the surgeon to remove these structures, which provide for a much less invasive procedure.

FIG. 5 shows that the cutting guide 108 can be configured with a third reference feature 260 and a fourth reference feature 264. The third reference feature 260 is disposed on the second side 204 of the cutting guide. The third reference feature 260 is disposed on a portion of the second side 204 that would be disposed over the tibia 14 when the cutting guide 108 is applied to the patient. The third reference feature 260 is disposed opposite the first reference feature 232. The first and third reference features 232, 260 can be disposed on medial and lateral sides, respectively, of the cutting guide 108. As discussed in more detail elsewhere herein, the reference features 232, 236, 260, 264 are each configured to engage corresponding reference bushings. The engagement is such that the engagement limits motion or locks or fixes in space the location of the cutting guide relative to the specific patient's bone. This has the benefit of providing custom preparation of the bone to enable greater certainty in the position in which prosthetic components will be disposed.

The third reference feature 260 comprises a protrusion 270 that protrudes from the second surface 208. The third reference feature 260 includes a first end 272 fixed to the surface 208 and a second end 276 disposed away from the first end 272 of the protrusion 270. The fourth reference feature 264 comprises a protrusion 280 that extends from the second surface 208. The fourth reference feature 264 includes a first end 284 fixed to the surface 208 and a second end 288 disposed away from the first end 284 of the protrusion 280. The protrusions 270, 280 are spaced apart and have a length such that when the cutting guide 108 is coupled with the third and fourth reference bushings 110, 112 the clearance gap G is provided between the second (e.g., posterior) surface 208 and the joint (e.g., ankle) bone. The protrusion 270, 280 can be provided at isolated positions to provide isolated contact with corresponding reference bushings 110, 112 or with bone references. The protrusions 270, 280 can be provided at discrete positions to provide spaced apart contact with corresponding reference bushings or bone references.

The third and fourth reference features 260, 264 are described as having projections or feet. The first and second reference features 232, 236 also have these structures though in the illustrated embodiment these reference features are shorter. Nevertheless as shown in FIG. 2 the clearance gap G is provided between the second (posterior) side 208 of the reference guide 108 and the bones around the ankle including in the area around the first and second reference features 232, 236.

FIG. 5 shows that the first and third reference features 232, 260 can be disposed on medial and lateral sides of the cutting guide 108. The first and third reference features 232, 260 can be disposed at an angle to each other. The angle can be defined between lumens disposed in the reference features 232, 260. For example the first reference feature 232 can have a first opening 290 located on the first side 202 of the guide 108 and a second opening 294 on the second side 208 of the cutting guide 108. A lumen extends from the first opening 290 to the second opening 294 along an axis. The third reference feature 260 can have a first opening 298 located on the first side 202 of the guide 108 and a second opening 302 on the second side 208 of the cutting guide 108. A lumen extends from the first opening 298 to the second opening 302 along an axis. As discussed further below the lumens in the first and third reference features 232, 260 can receive the fixation pins 160 to secure the cutting guide 108 to the bone portions adjacent to the joint. The lumens in the first and third reference features 232, 260 can be angled to each other to help secure the orientation of the cutting guide 108 relative to the bone portions. In other embodiments these lumen may guide screws rather than pins to securely attach to reference bushing that have mating internal threads.

FIG. 5 shows that the cutting guide 108 can have four reference features. The second reference feature 236 can have a first opening 310 located on the first side 202 of the guide 108 and a second opening 314 on the second side 208 of the cutting guide 108. A lumen extends from the first opening 310 to the second opening 214 along an axis. The fourth reference feature 280 can have a first opening 322 located on the first side 202 of the guide 108 and a second opening 326 on the second side 208 of the cutting guide 108.

A lumen extends from the first opening 322 to the second opening 326 along an axis. The second and fourth reference features 236, 260 can be disposed on medial and lateral sides respectively of the cutting guide 108. The lumen of the second reference feature 236 can be disposed at an angle to the lumen of the fourth reference feature 260. The angle between the lumens of the second and fourth reference features 236, 260 can help to immobilize the cutting block relative to the bone portions around the ankle joint. In other embodiments these lumen may guide screws rather than pins to securely attach to reference bushing that have mating internal threads.

The cutting guide 108 can be made for a specific patient based on spatial location information gathered from the patient, as discussed further below. Although patient specific cutting guides are known, such devices generally require complex surface contours to allow the cutting guide to be placed directly on the bone to immobilize the cutting guides in the proper position on the bone. In contrast, the cutting guide 108 is made to provide a clearance gap G (see FIG. 10) between the bone and soft tissue over the ankle joint and the second side 204, e.g., between bone and soft tissue and the second surface 208. The clearance gap takes into account the patient's soft tissue and bony structure of the joint. Because the cutting guide 108 is configured to be spaced from the bony structure the contour or shape of the second surface 208 can be relatively simple, e.g., two planar portions as discussed below. In many patients some minimal interaction with the tissue may not impact the accuracy of placement of the cutting guide as soft tissue is normally at least somewhat compressible or displaceable. In some embodiments, the gap G is sufficient to completely prevent interactions with soft tissue as well. The guide 108 could be configured with a more complex second surface 208 to match that of the tissue surface to aid in minimizing or avoiding any tissue contact. Also, it in envisioned that in alternate embodiments, the reference bushings 104, 106, 110, and 112 can be compatible with other patient specific cutting guides or blocks, in one non-limiting example, reference bushings can be provided to matingly engage with the Prophecy® Infinity® Alignment Guide (manufactured by Wright Medical Technology, Inc, Memphis TN)

In various embodiments, the cutting guide 108 offers a simple overall construction. For example, the second surface 208 comprises a first portion 340 configured to be disposed in close proximity to but not in contact with a neck of a talus and a second portion 344 configured to be disposed in close proximity to but not in contact with an anterior face of a tibia. The first and second portions 340, 344 can have a form that is entirely independent of the shape of the tibia and talus. The first and second portions 340, 344 can have a relatively simple form, for example being generally planar as shown in FIG. 2. The first portion 340 can be disposed in a first plane and the second portion 344 can be disposed in a second plane. The second plane can be disposed at an angle relative to the first plane, as showing in FIG. 2. The patient specific interaction of the cutting guide 108 is provided by the first and second reference features 232, 236 and by the third and fourth reference features 260, 264. The first reference feature 232 and the third reference feature 260 are disposed on the first portion 340 of the second surface 208. The second reference feature 236 and the fourth reference feature 264 are disposed on the second portion 344 of the second surface 208. The length of the reference features, e.g., the protrusions, enable the cutting guide 108 to mate with the reference bushings 104, 106, 110, 112 in a prescribed manner. The prescribed manner results in the cutting feature 216 (and other cutting features of the cutting guide 108) being disposed at a prescribed distal-proximal location as well as at a prescribed varus-valgus angle. These and other prescribed features can be used to prepare the bones of a patient or without deformity or with deformity as discussed below.

Methods

Figure 6:
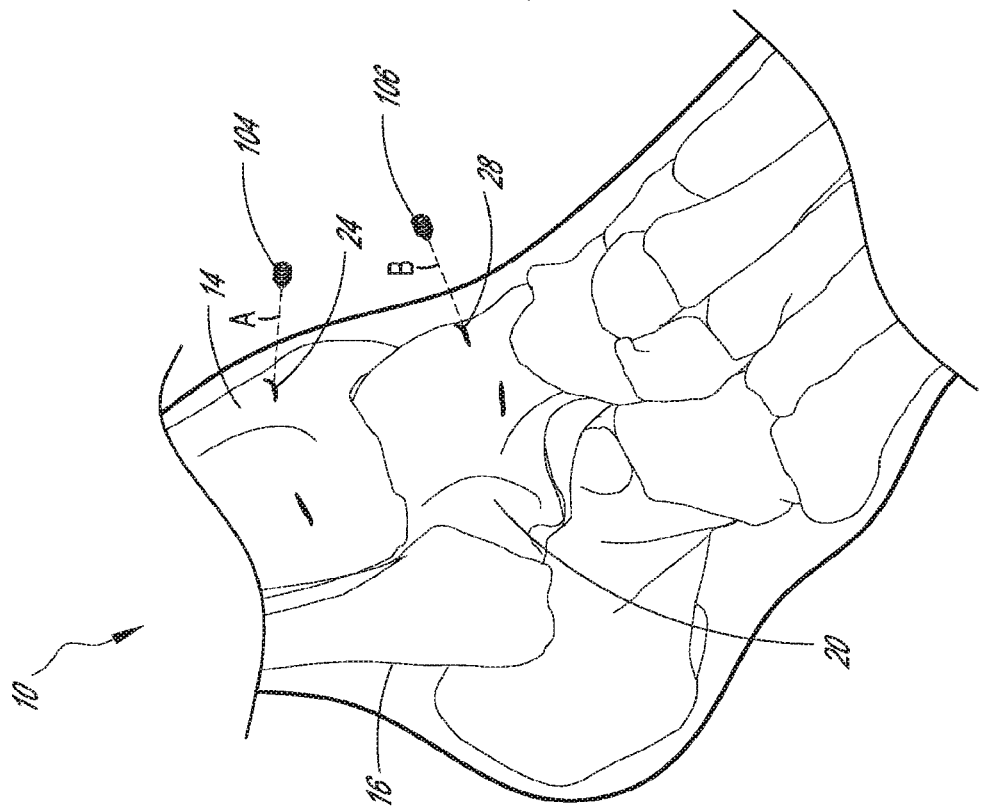
FIG. 6 illustrates a portion of a method showing the location of the reference bushings in the tibia and in the talus of a patient.

FIGS. 6-11 illustrate various embodiments of joint surgery methods made possible by the bone preparation system 100. In FIG. 6, a portion of each of the bones of the ankle joint is exposed. The bone portions are exposed by forming one or more stab incisions in the skin. In the illustrated method, a first incision 24 is made above a first bone portion, such as a distal anterior aspect of the tibia 14. A second incision 28 is made across a second bone portion, such as a neck of the talus 20. A path is cleared from the first incision 24 to the distal anterior aspect of the tibia 14. A path is cleared from the second incision 28 to the distal anterior aspect of the talus 20. In another method a single incision exposes both the tibia 14 and the talus 20.

After access is provided to the tibia 14, the first bushing 104 is advanced into the tibia adjacent to the ankle joint 10. After access is provided to the tibia 14, the second bushing 106 is advanced into the talus 20 adjacent to the ankle joint 10. The first and second bushings 104, 106 can be advanced through a single incision that spans from a portion of the tibia 14 to a portion of the talus 20. In some embodiments, a cannula (not shown) is inserted through each of the incisions. The cannula can be an elongate hollow tubular body with sufficient wall strength to remain open while holding the soft tissues between the skin and the bone out of the lumen of the cannula. The cannula can be disposed along the axes A, B shown in FIG. 6. More specifically, a first cannula can be placed along the axis A through the first incision 24 such that a distal end of the first cannula is adjacent to the anterior surface of the tibia 14 and a proximal end of the first cannula is outside of the skin of the patient. A second cannula can be placed along the axis B through the second incision 28 such that a distal end of the second cannula is adjacent to the neck of the talus 20 and a proximal end of the second cannula is outside of the skin of the patient. The reference bushing 104 is advanced through the first cannula 24. The second reference bushing 106 is advanced through the second cannula 28.

FIG. 6 shows a method in which the third reference bushing 110 and the fourth reference bushing 112 have also been placed in the tibia 10 and talus 20 respectively. After the four bushings 104, 106, 110, 112 are placed the cannula or cannulae (if used) can be removed.

FIG. 7 shows that after the bushings have been positioned in the tibia 14 and the talus 20, spatial location information is obtained. The spatial location information can include the location and orientation of the first reference bushing 104 and a portion of the tibia 14 around the first reference bushing 104. The spatial location information can include the location and orientation of the second reference bushing 106 and a portion of the talus 20 around the second reference bushing 106. Spatial location information is obtained from the third reference bushing 110 if present and the tibia 14. Spatial location information is obtained from the fourth reference bushing 112 if present and the talus 20. The spatial information can be obtained by any of a variety of methods. For example, spatial location information can be obtained from a CT scan after one or a plurality of reference bushings are placed in the tibia 14 and the talus 20. Spatial location information can be obtained by any three dimensional imaging or profiling technology. Spatial location information could be obtained by mechanically tracing a surface of the bone and or probing the bushings.

After the spatial location information is collected by the CT scan or other imaging or probing apparatus, the cutting guide 108 is formed or created based on the spatial location information. In the method, spatial location information generated by a CT scan includes a position of at least two reference bushings, e.g., two, three, or four of the bushings 104, 106, 110, 112. The spatial location information is received by a system that is adapted to create or form the patient specific cutting guide 108. The information can include spatial information about the location of at least two bone portions. For example, the bone locations can include distal and anterior surfaces of the tibia 14, the fibula 16, and/or the neck of the talus 20. The cutting guide 108 can be formed based upon the spatial location information that is received. When the cutting guide 108 is formed in this manner, the location of the cutting features 216, 218 relative to at least one of the bone portions is established and incorporated into the structure of the cutting guide 108. When the cutting guide 108 is mated with the reference bushings 104, 106, 110, 112 the cutting features 216, 218 are properly located to make appropriate cuts to properly position an ankle implant component.

Because the preparation of the cutting guide 108 can take a few hours to a few days or weeks, the ankle prosthesis procedure can have multiple stages. A first stage involves placing the bushings 104, 106, 110, 112. A second stage, which can be combined with the first stage in some cases, involves obtaining the spatial location information. A third stage involves creating the cutting guide 108, which may be customized to the patient in view of the spatial location information.

In one method, forming the cutting guide 108 includes forming the first reference member 232 to mate with the first reference bushing 104 and forming the second reference member 236 to mate with the second reference bushing 106. Forming the cutting guide 108 includes forming the third reference member 260 to mate with the third reference bushing 110 and forming the fourth reference member 264 to mate with the fourth reference bushing 112. The reference members 232, 236, 260, 264 are formed to have a length sufficient to create clearance from the bone, as discussed above, when the reference members are so mated. The references bushings 104, 106, 110, 112 will generally already be placed in the patient's bones when the fabrication of the cutting guide 108 is taking place.

When the cutting guide 108 has been formed the cutting guide 108 can be used on the patient in a fourth stage of a method to modify the bones around the joint to prepare the bones to be mated with a prosthesis. The cutting guide 108 can be used on the patient for whom it was made to perform a precise prosthesis implantation procedure. In one technique, the reference bushing 104 is previously placed on a medial side of the patient's distal, anterior tibia 14. The reference bushing 106 is previously placed in a medial side of the neck of the talus 20. The reference bushing 110 is previously placed in a lateral side of the distal, anterior tibia 14. The reference bushing 112 is previously placed in a lateral side of the neck of the talus 20.

Thereafter, in one technique the second reference feature 236 of the cutting guide 108 is connected to the reference bushing 106. The connection initially is that a distal aspect of the second reference feature 236 is inserted into the motion limiting portion 172 of the reference bushing 106. A convex surface at the free end of the second reference feature 236 can be mated with the concave surface 176. As discussed above, the mating between the reference feature 236 and the concave surface 176 can include or be substituted for other sorts of contact or mating. A snap-fit mating, as described above and further below, could be provided between the reference feature 236 and the concave surface 176. Also, although the surface 176 is described as being concave and receiving the reference feature 236, bushing 106 could have a convex proximal end that receives a concave distal end portion of the reference feature 236. More generally, any of the reference bushings can be modified to have a convex proximal portion that is received within a concave distal portion of a corresponding reference feature. In alternate embodiments, any of the reference bushings can be modified to have a male taper (e.g., a Morse taper) proximal portion. The male taper proximal portion can be received within a distal portion of a corresponding reference feature (e.g., within a tapered recess, concave area, or female component). Also, the mating subsequently can be augmented by placing a pin or screw into and/or through axially aligned lumens through the reference feature 236 and the bushing 106. Thereafter, a similar connection is provided between a convex surface of the third reference feature 260 and the motion limiting portion 172 of the reference bushing 112. The mating can subsequently be augmented by placing a pin or screw into and/or through axially aligned lumens through the reference feature 260 and the bushing 112. The locations of the reference features 236, 260 relative to the talus 20 are pre-defined by the patient specific nature of the cutting guide 108. Preferably the second side 208 of the cutting guide 108 is spaced apart from the talus 20 at locations spaced away from the reference features 236, 260, for example along a path extending medially and laterally between the reference bushings 106, 112. The spacing allows the placement of the cutting guide 108 such that the soft tissues and bone need not be removed or disrupted but yet the location of the cutting feature 216 and other aspects of the cutting guide 108 relative to the talus 20 are as expected based on the spatial location information that was used to form the cutting guide 108.

Figure 8:
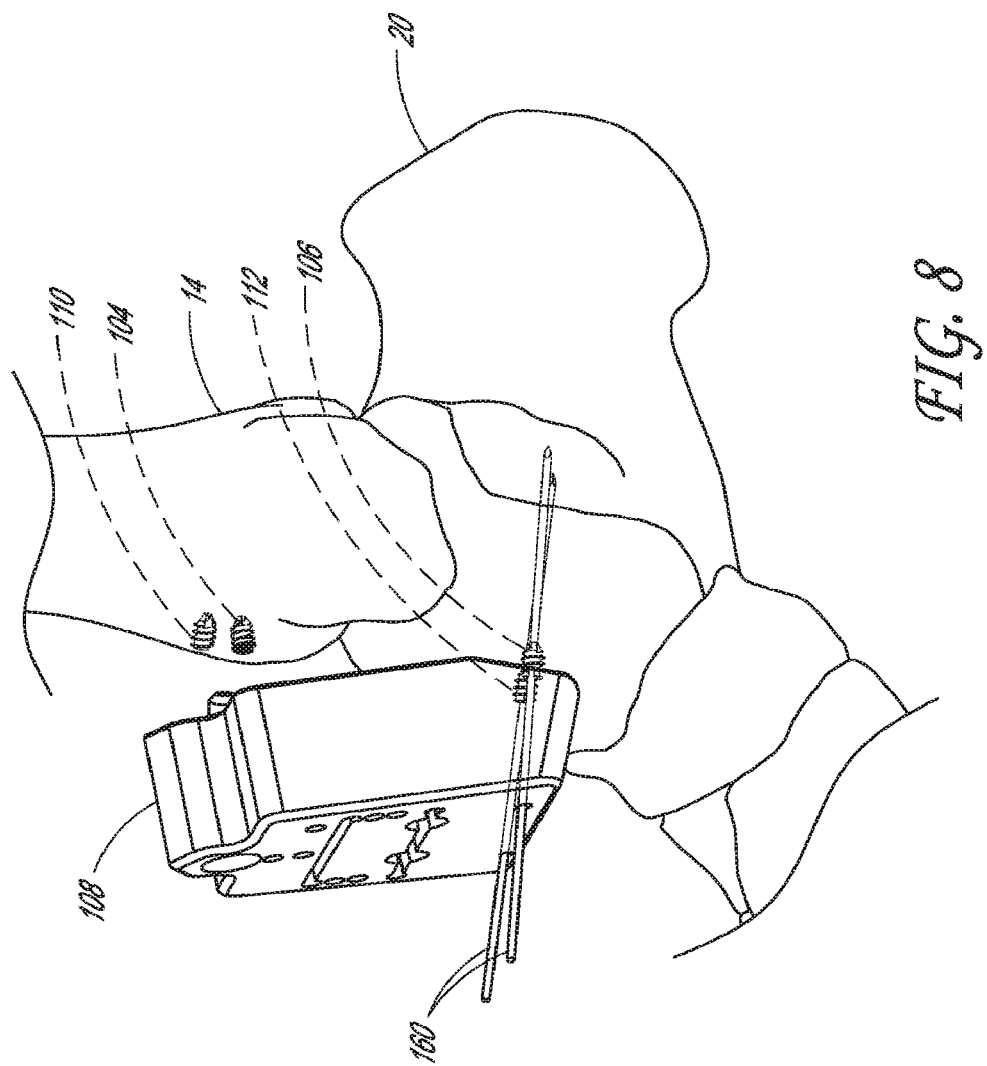
FIG. 8 illustrates a portion of a method in which a cutting guide has been secured to a talus, the talus placed in plantar flexion.

FIG. 8 shows that the connection between the cutting guide 108 and the talus 20 can be made more secure by advancing a fixation pin 160 into the opening 310 through the cutting block 108 and the reference bushing 106 and into the medial side of the neck of the talus 20. The connection can be further more secure by advancing a fixation pin 160 into the opening 322, through the cutting guide 108 and reference bushing 112 and into the lateral side of the neck of the talus 20. A screw could be used in place of one or both of the pins 160. In embodiments with a snap-fit connection, the pins 160 may not be needed. Snap-fit connections and the pins 160 could be used together to provide a lesser initial connection followed by a more secure connection for later phases of the procedure where greater security is needed, e.g., when a saw is disposed through the guide 108 and acting on the bone. In some cases further connection is provided by other devices such as screws 340. In the illustrated embodiment opening 342 adjacent to the distal cutting feature 216 provide access for the screw 340 to be advanced through the cutting guide 108 and into the talus 20.

FIG. 8 shows that in one technique the ankle 10 is placed plantar flexion to facilitate connecting the cutting guide 108 to the talus 20. Positioning the ankle 10 in plantar flexion exposes a greater area of the neck of the talus 20 such that the cutting guide 108 can be secured to the bone. While the ankle joint is in plantar flexion, the patient specific cutting guide 108 is rigidly connected to the talus 20 with the fixation pins 160 and/or screws 340, as discussed above.

Figure 9:
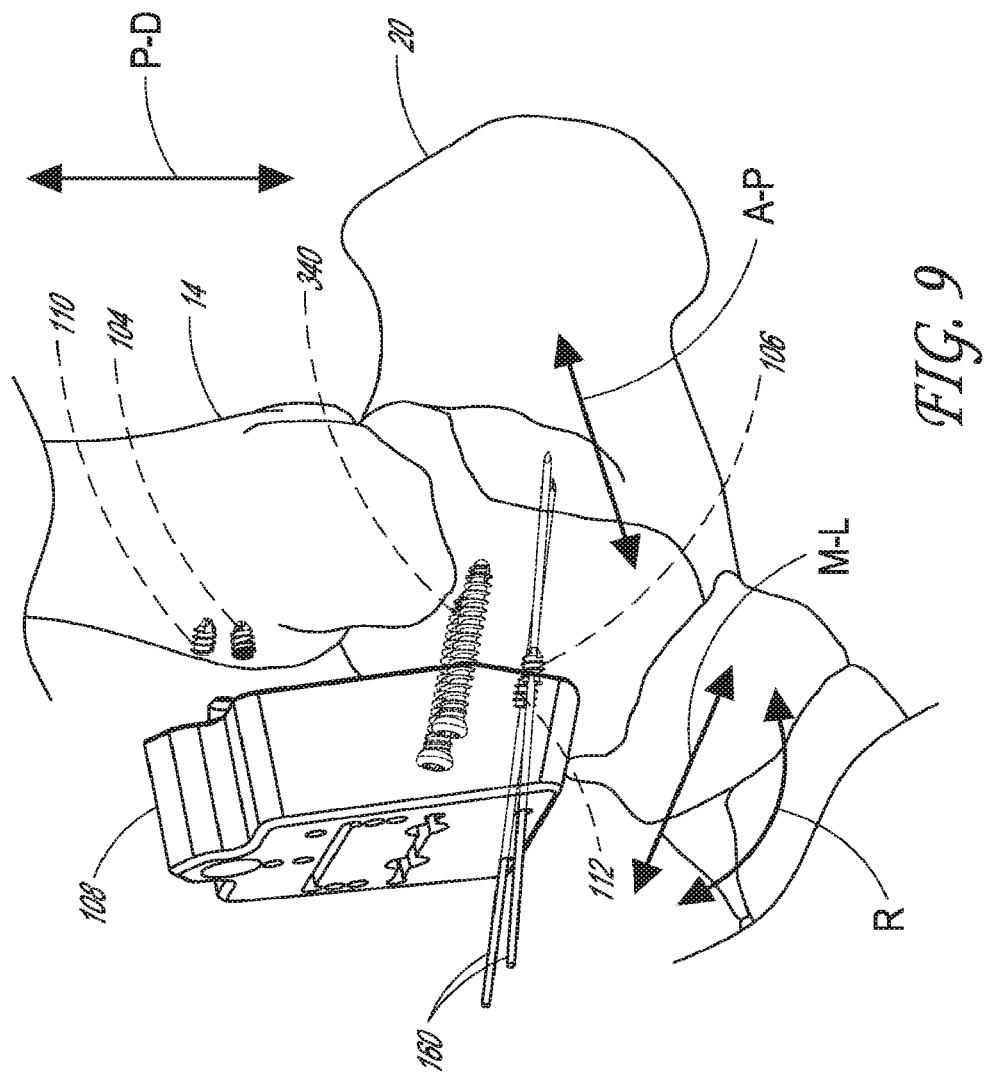
FIG. 9 illustrates a portion of a method in which a cutting guide is preparing to contact the tibia and thereby correcting desired deformities.

FIG. 9 shows that after the cutting guide 108 is rigidly connected to the talus 20, motion of the talus relative to the tibia 14 and/or the fibula 16 can be provided. Such corrective motion can be provided in a varus/valgus direction as indicated by the arrow R. Such motion can be provided in a proximal distal direction as indicated by an arrow labeled P-D. Such motion can be provided in an anterior-posterior direction as indicated by an arrow labeled A-P. Such motion can be provided in a medial/lateral direction as indicated by an arrow M-L. These motions can be combined in complex ways and can be prescribed by the form of the cutting guide 108 to alleviate one or more forms of deformity.

Figure 10:
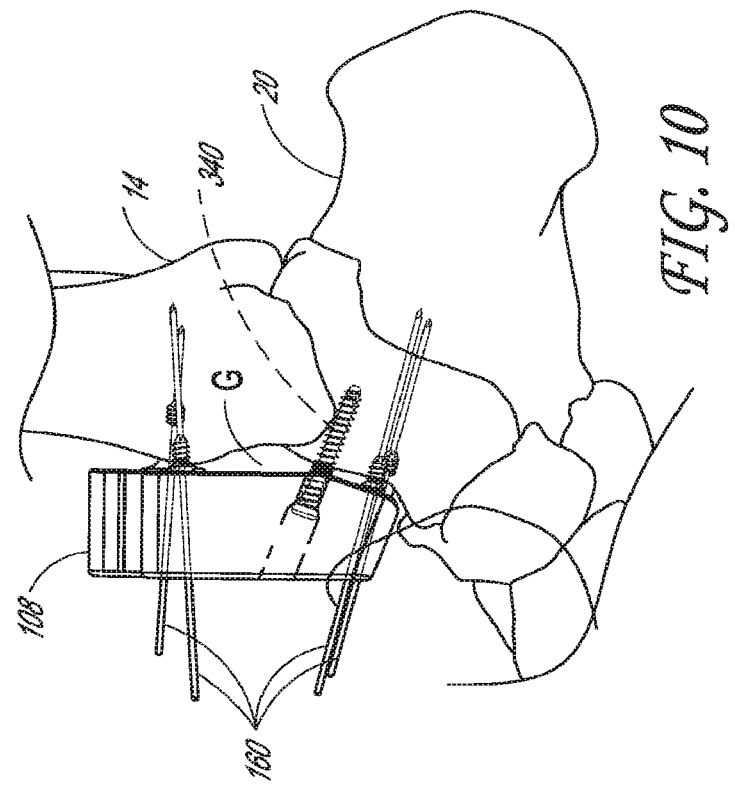
FIG. 10 illustrates a portion of a method in which a cutting guide is secured to the tibia and to the talus in a position to guide bone cuts to enable an implant to be properly placed, including in some embodiments automatically correcting deformity.

Whether the motion out of plantar flexion is by rotation or other motion, the motion of the cutting guide 108 causes the first reference feature 232 to contact and to be engaged with the first reference bushing 104. Such motion can continue until the third reference feature 260 contacts and is engaged with the third reference bushing 110. FIG. 10 shows that a rigid connection between the cutting guide 108 and the tibia 14 can be provided in a suitable manner, such as by advancing fixation pins 160 into the openings 290, 298, through the reference bushings 104, 110 and into the tibia 14.

Figure 11:
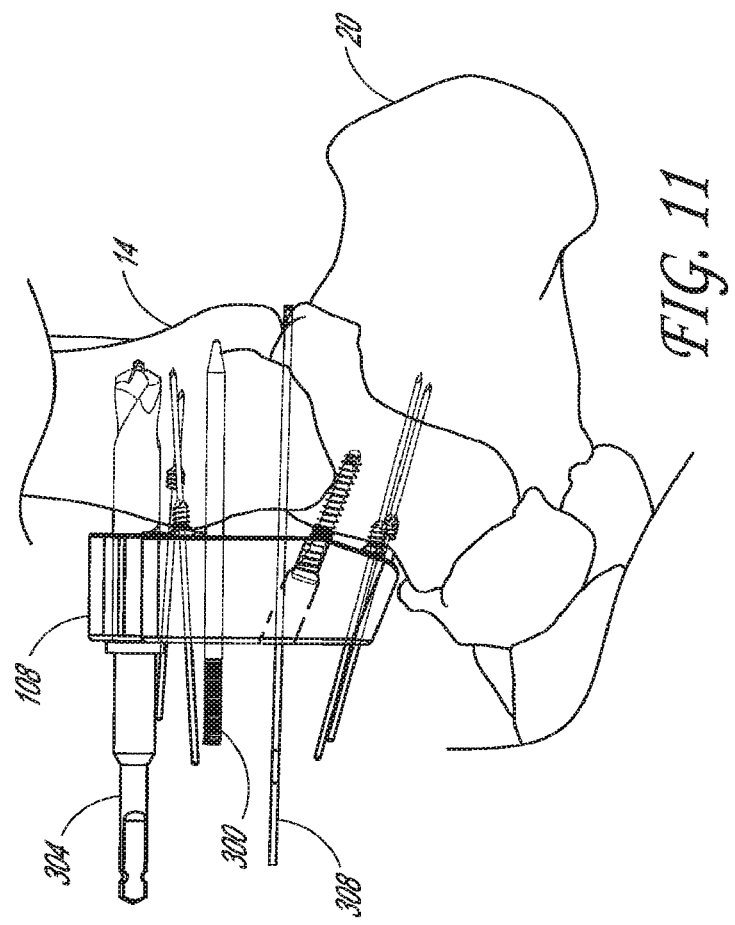
FIG. 11 illustrates a portion of a method in which the bone is being prepared to receive an ankle prosthesis.

FIG. 11 shows that thereafter pins 300, reamers 304, and saw blades 308 can be advanced through the cutting guide 108 to prepare the tibia 14 or other bone portion.

The bushings 104, 106, 110, 112 can be configured to be left in place or removed. In some embodiments, the methods involve removing the bushings from the bone(s) around the joint after the bones have been prepared to receive a prosthesis. In some embodiment, the bushings 104, 106, 110, 112 are small and their placement is away from the joint and sensitive soft tissue such that they may be left in place after the procedure without any impact on the patient. In other embodiments, the bushings 104, 106, 110, 112 may be configured to be bioabsorbed into the patient and thus can be left in place but will not remain permanently in the patient.

In certain embodiments, the reference features 232, 236, 260, 264 are configured to mate with bone references, in the form of passages that are formed in, e.g., drilled into, the bone(s) around the joint. As such, there is no need to remove bushings or to confirm the efficacy of permanent retention thereof in the bone. Such drilled holes can simply heal over time and thus have no permanent impact on the patient.

Figure 12:
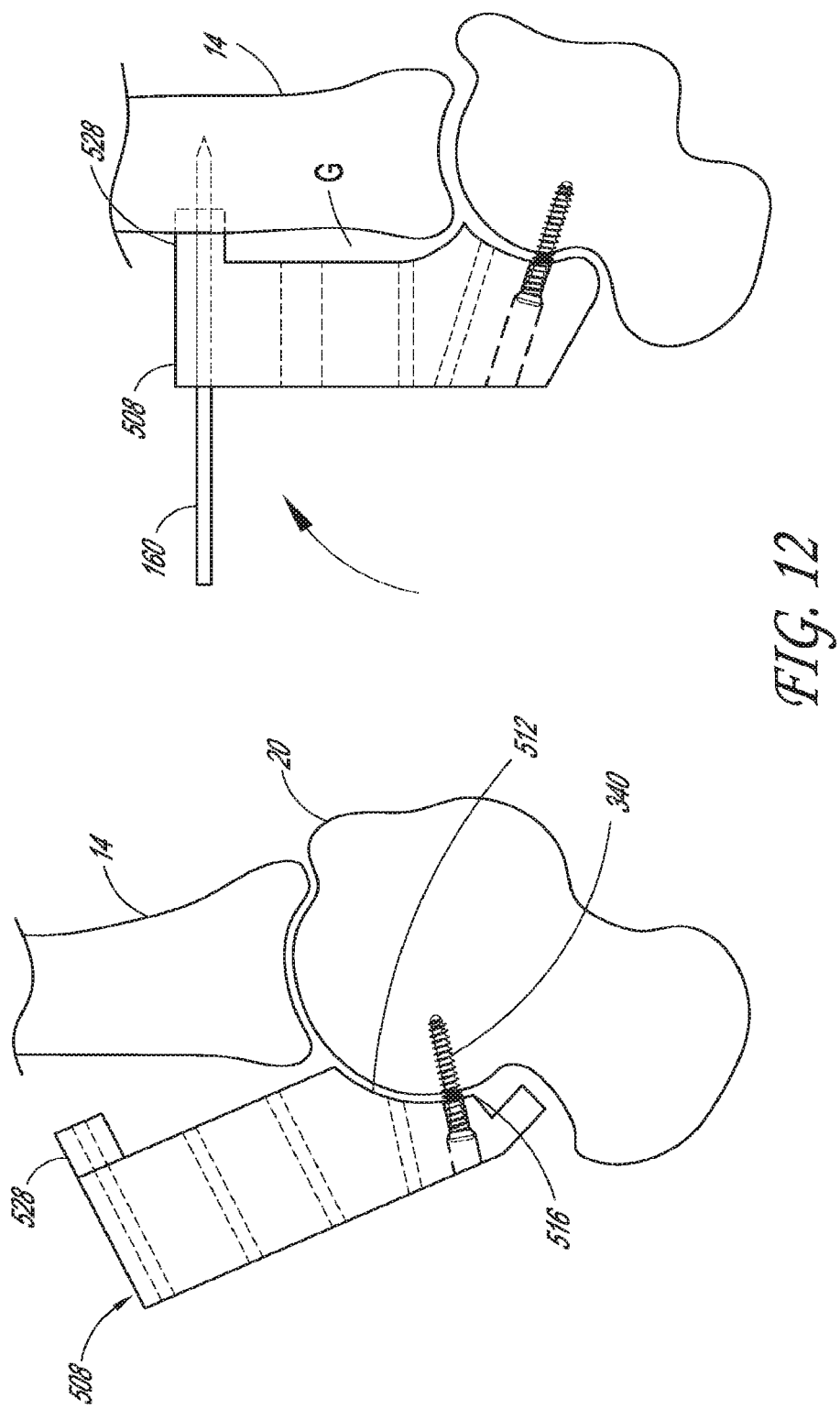
FIG. 12 shows a modified embodiment of an ankle prosthesis bone preparation system and a method of using the system.

FIG. 12 shows an alternative embodiment in which a cutting guide 508 can be provided that includes a distal portion 512 to be mated with a neck of the talus 20. The distal portion can be mated by advancing a screw 340 therethrough. The screw 340 can be advanced along a lumen of the cutting guide 508 defined by spatial location information of the talus 20, e.g., of a bone reference 516 of the talus. The bone reference 516 can be an opening formed in the talus 20. The bone reference 516 can be a bony prominence or a natural landmark. In some embodiments the distal portion 512 has a bone engaging surface that is formed to match that of the neck of the talus 20. A proximal portion 520 of the cutting guide 508 can include a reference protrusion 528. The reference protrusion 528 can be configured to mate with a bone reference, e.g., an opening formed in the tibia 14, a bony prominence or a natural landmark of the tibia 14. A fixation pin 160 can be advanced through the reference protrusion 528 to secure the cutting block 508. The reference protrusion 528 enables the cutting guide 508 to mate with the tibia while maintaining a clearance gap G at least in the region of the tibia. By providing the gap G, many of the advantages described herein are attained, at least as to the tibia 14.

Figure 13:
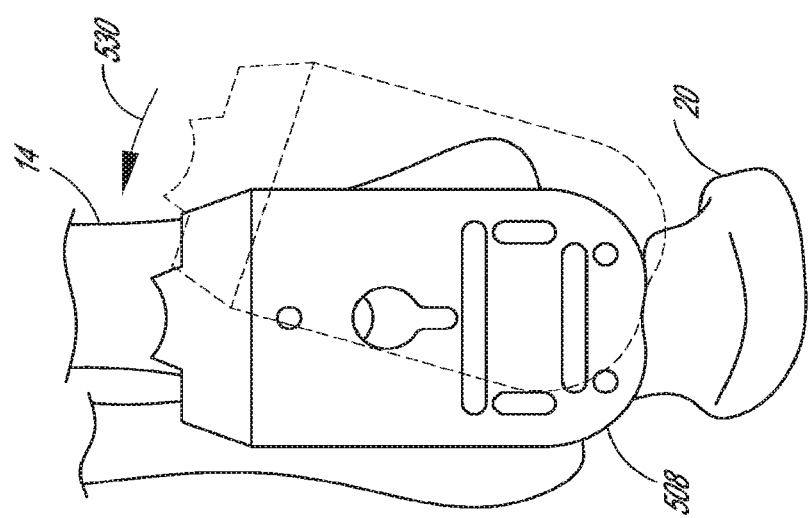
FIG. 13 shows a method of using the system of FIG. 12 to automatically correct deformities in an ankle joint.

FIG. 13 illustrates using the cutting guide 508 to correct the deformity illustrated in FIG. 1A. The deformity is corrected by first coupling the distal portion 512 with the neck of the talus 20. Thereafter a rotation described by the arrow 530 is provided. The rotation takes the cutting guide 508 from the dashed line position to the solid line position of FIG. 13. This causes the deformity illustrated in FIG. 1A to be corrected by raising and aligning (as in FIG. 1B) the talus 20 with the tibia 14 of the ankle joint 10.

Figure 14:
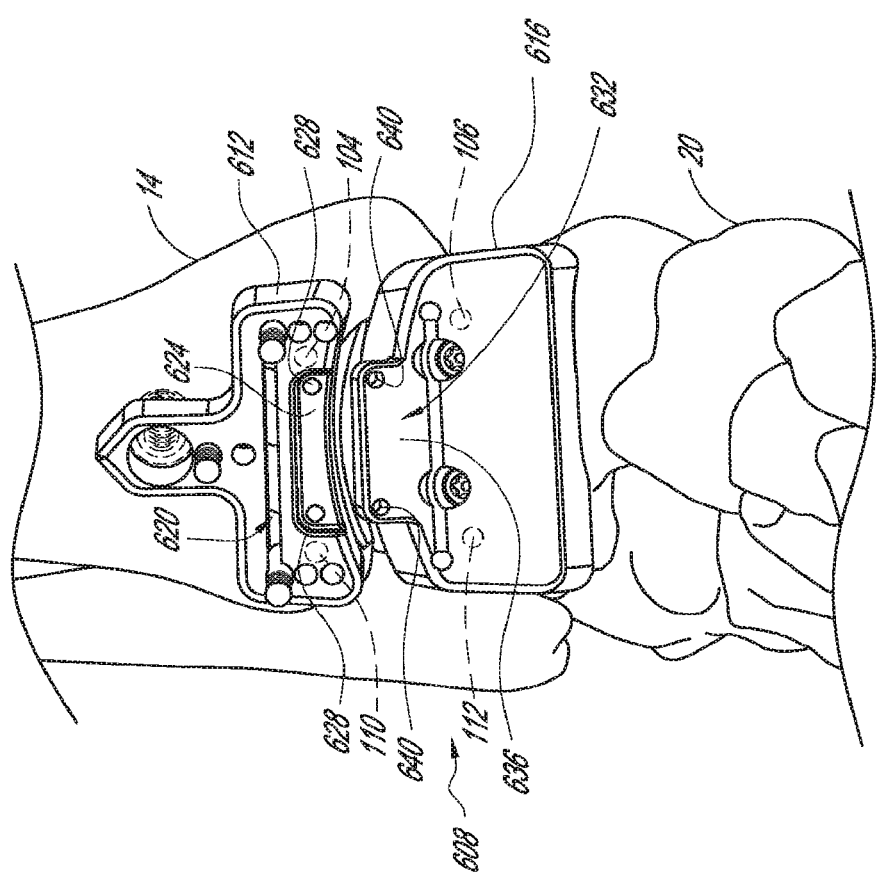
FIG. 14 illustrates another embodiments of a patient specific guide in which the guide comprises two separable portions.

FIG. 14 shows a cutting guide system 608 having two separable guides, in which the proximal guide attaches individually to the proximal bone, and the distal guide attaches individually to the distal bone. These guides can be formed at least partially according to the methods described herein. Specifically, a plurality of bone references, e.g., a combination of one or more of a plurality of references bushings and a plurality of natural or surgeon formed landmarks, such as bony prominences, divots, or holes formed in the bone is provided and/or identified. FIG. 14 shows the reference bushings 104, 106, 110, 112 in dashed lines. Three dimensional spatial location information is gathered, e.g., using CT scans, traces, or other similar technologies. A multi piece cutting guide 608 is designed and manufactured that preferably is patient specific. The cutting guide 608 includes a first block 612 configured to couple with the tibia 14. In one embodiment, the first block 612 is coupled with the tibia 14 by first contacting the reference bushings 104, 110. Thereafter any securement method described herein can be used to rigidly connect the first block 612 to the tibia 14. The cutting guide 608 includes a second block 616 configured to couple with the talus 20. In one embodiment, the second block 616 is coupled with the talus 20 by first contacting the reference bushings 106, 112. Thereafter any securement method described herein can be used to rigidly connect the second block 616 to the talus 20.

The first block 612 has a first interface portion 620 disposed on a distal portion 624 thereof. The distal portion 624 can be on a distal face or can be on an anterior face, e.g., extending proximally from a distal face of the first block 612. The first interface portion 620 can also include one or a plurality of apertures 628 formed in the distal portion 624. The second block 616 can have a second interface portion 632 disposed on a proximal portion 636. The proximal portion 636 can be on a proximal face or can be on an anterior face, e.g., extending distally from a proximal distal face of the second block 616. The second interface portion 632 can also include one or a plurality of apertures 640 formed in the proximal portion 636.

The first and second interface portions 620, 632 are configured to mate to provide a spatial position of the tibia 14 and the talus 20. For example the first and second blocks 612, 616 can be configured such that when the interface portions 620, 632 are mated cutting features, which are similar to any of the described above and which are formed on and through the cutting guide 608, are properly positioned and oriented. In one embodiment, the first interface portion 620 comprises a concave recess that is open on a distal face of the first block 612. The recess extends only partly through the thickness of the first block 612 from the anterior face thereof. The second interface portion 632 includes a proximally extending protrusion on the second block 616 that is configured to be received in the concave recess of the first block 612. The first and second blocks 612, 616 can be secured together by any suitable means, such as by advancing pins through the apertures 640 and into the apertures 628.

The first block 612 can have reference features similar to the reference features 232, 260. The second block 616 can have reference features similar to the reference features 236, 264. The first block 612 is shown with fixation pins 160 extending into openings similar to the openings 290, 298. The second block 616 is shown with fasteners 350 securing the second block 616 to the talus. Accordingly, the second block 616 can be configured to be positioned on the talus 20 in a variety of ways. The fasteners 350 can be advanced through reference bushings or similar features to secure the second block 616 in a predefined position relative to the talus 20 and/or the ankle 10. The second block 616 could have openings similar to the openings 310, 322 for advancement of fixation pins 160 through the second block 616 and through a bone reference, such as the reference bushings 106, 112. In some methods, it is sufficient to provide a patient specific interface to one of the blocks 612, 612 (e.g., to the first block 612) and to permit the other block (e.g., the second block 616) to be placed by a less precise method.

After the first and second blocks 612, 616 are secured to the tibia 14 and talus 20 respectively, relative motion is provided between the talus 20 or foot and the tibia 14 or lower leg. Such movement continues until the second interface portion 632 is engaged with, e.g., is received in, the first interface portion 620. Thereafter, the portions 620, 632 are secured together. For example, a pin can be advanced through the openings 640 and into the opening 628. When the first and second blocks 612, 616 are so engaged, the talus 20 will be properly positioned relative to the tibia 14. The proper positioning of the first and second blocks 612, 616 can result in a correction of any deformity in the ankle. For example, when so engaged, the varus/valgus deformity of FIG. 1A will be reduced or eliminated as shown in FIG. 1B.

Figure 16:
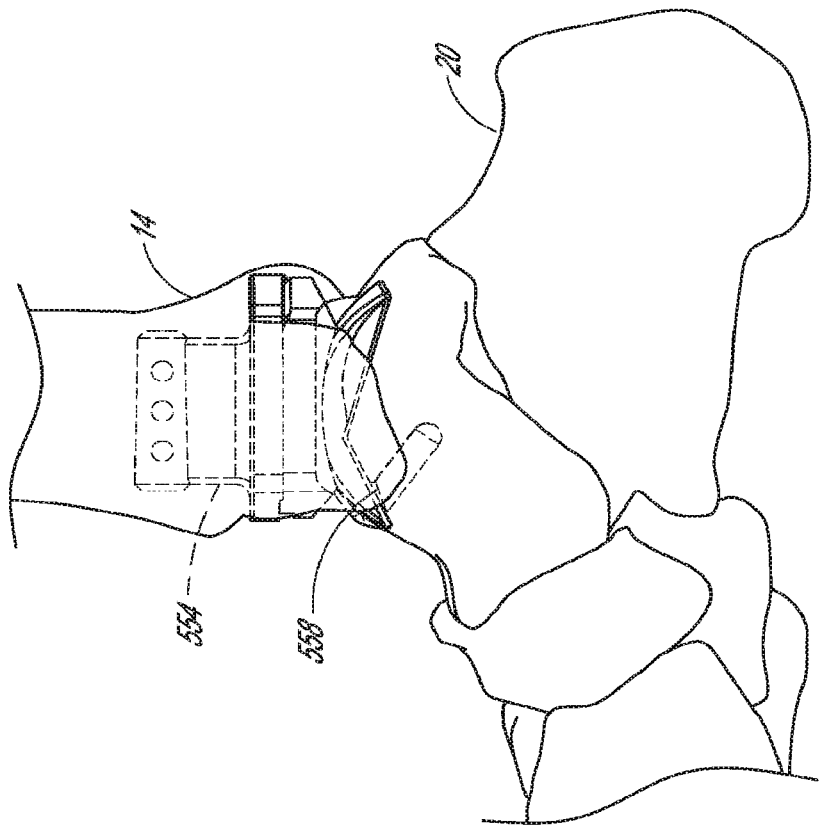
FIG. 16 shows a lateral view of the ankle prosthesis coupled with the tibia.
Figure 15:
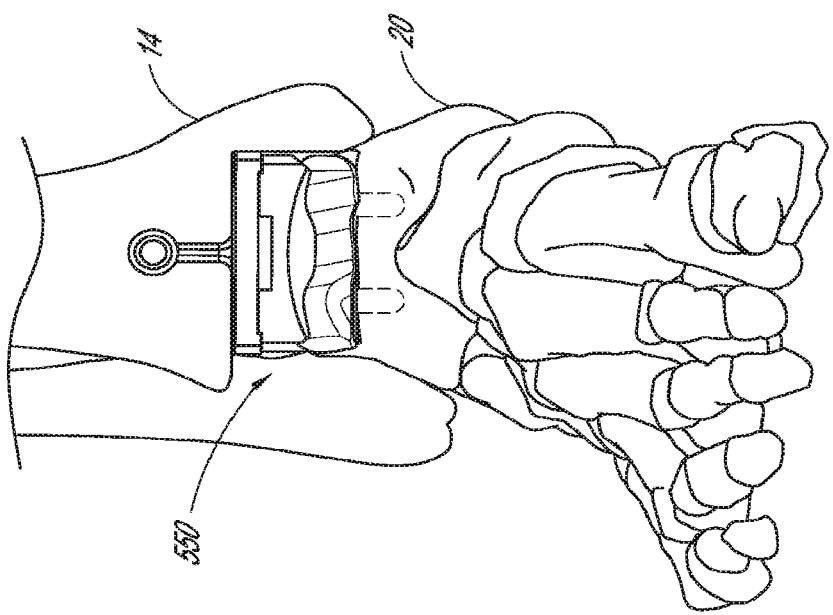
FIG. 15 shows an anterior view of an ankle prosthesis coupled with the tibia and the talus.

FIGS. 15 and 16 show that after using any of the cutting guides herein to prepare an ankle joint, a prosthesis 550 can be placed in the joint space. The prosthesis 550 can include a proximal portion 554 coupled with the talus 20 and a distal portion 558 coupled with the tibia 14. The proximal and distal portions 554, 558 articulate over each other to restore normal and pain free function to the ankle joint 10.

Additional Embodiments and Methods

Figure 17:
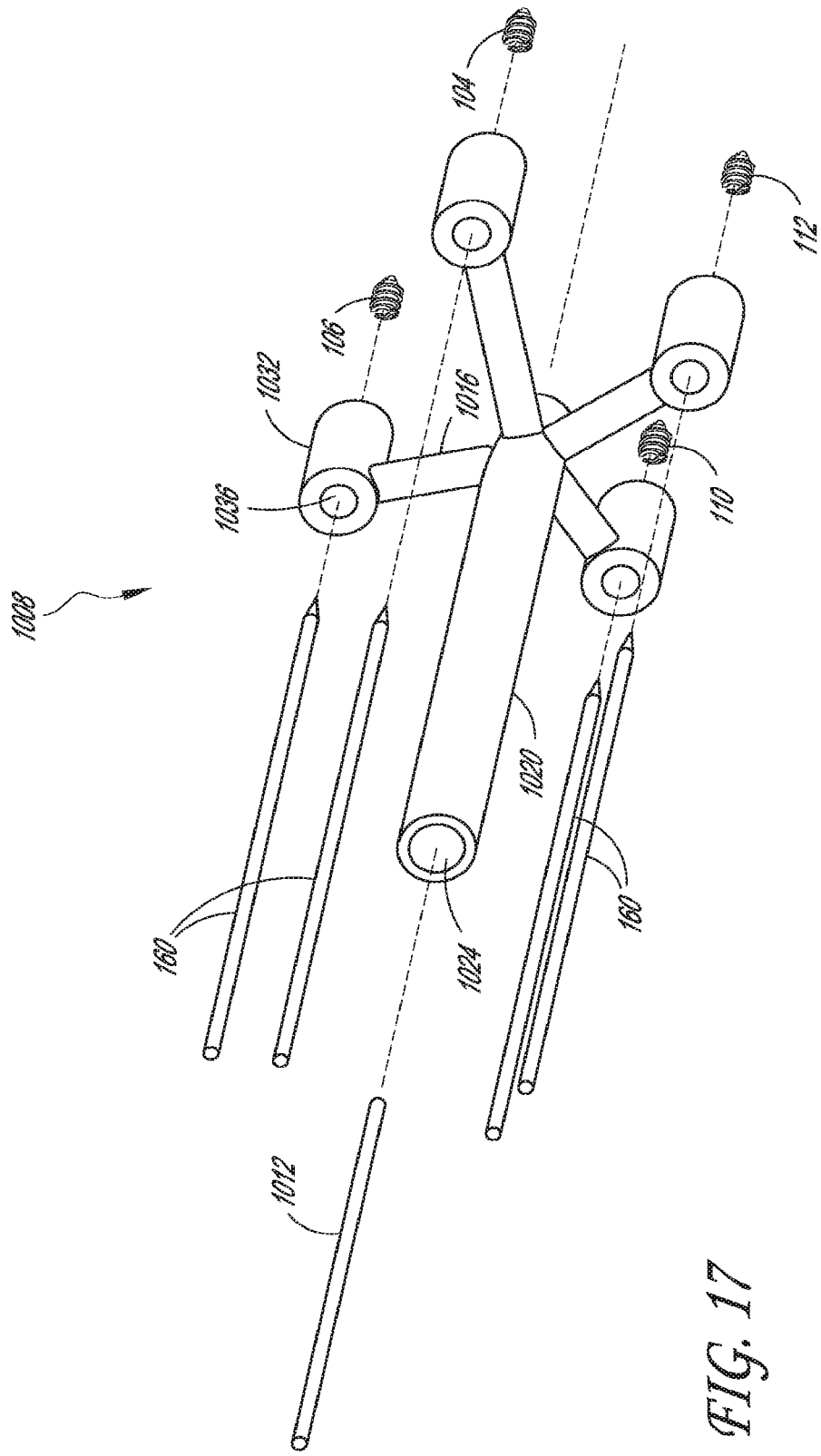
FIG. 17 is an exploded view of a shoulder preparation system.
Figure 18:
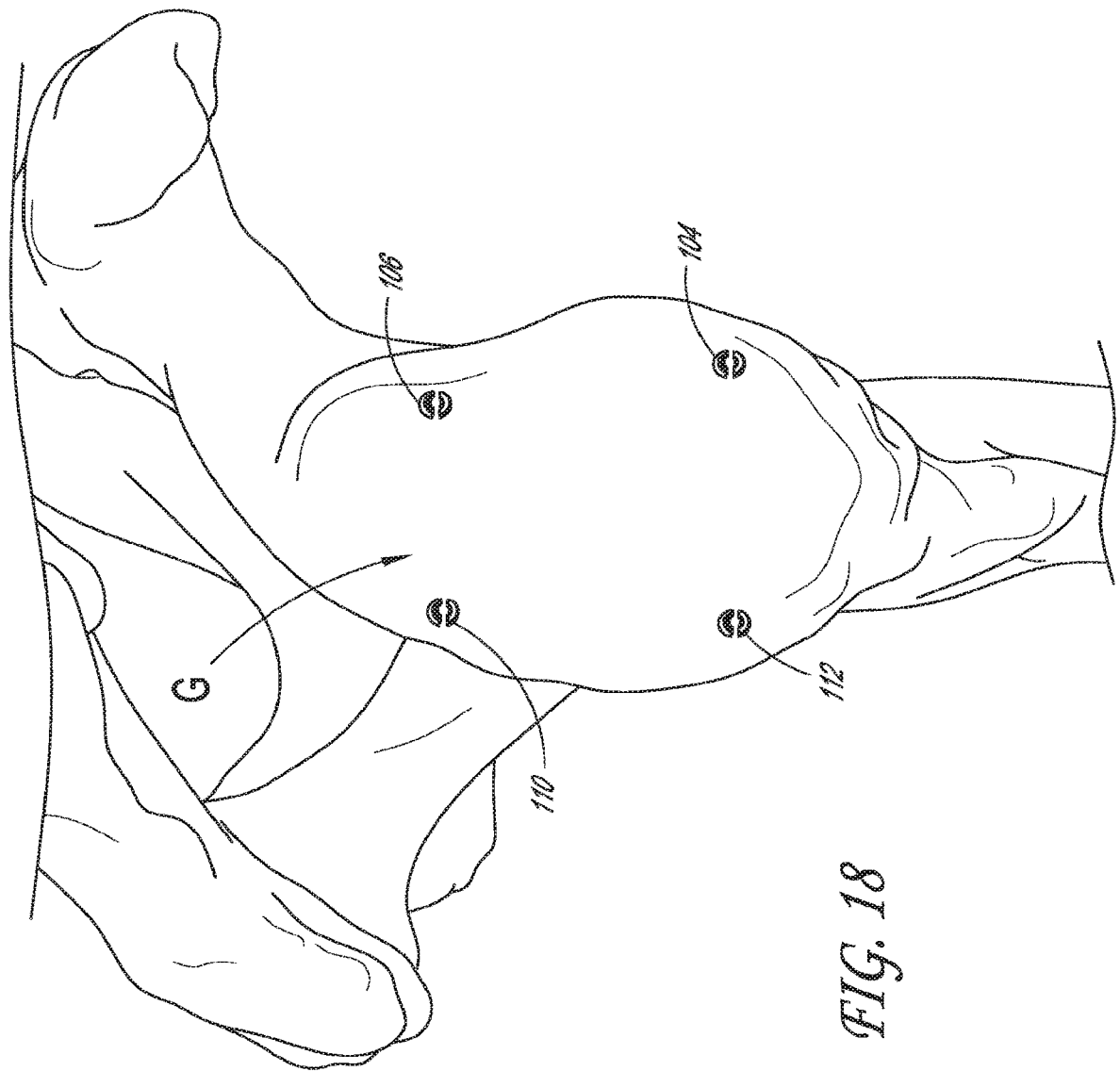
FIG. 18 shows a glenoid surface into which reference bushings have been placed.
Figure 19:
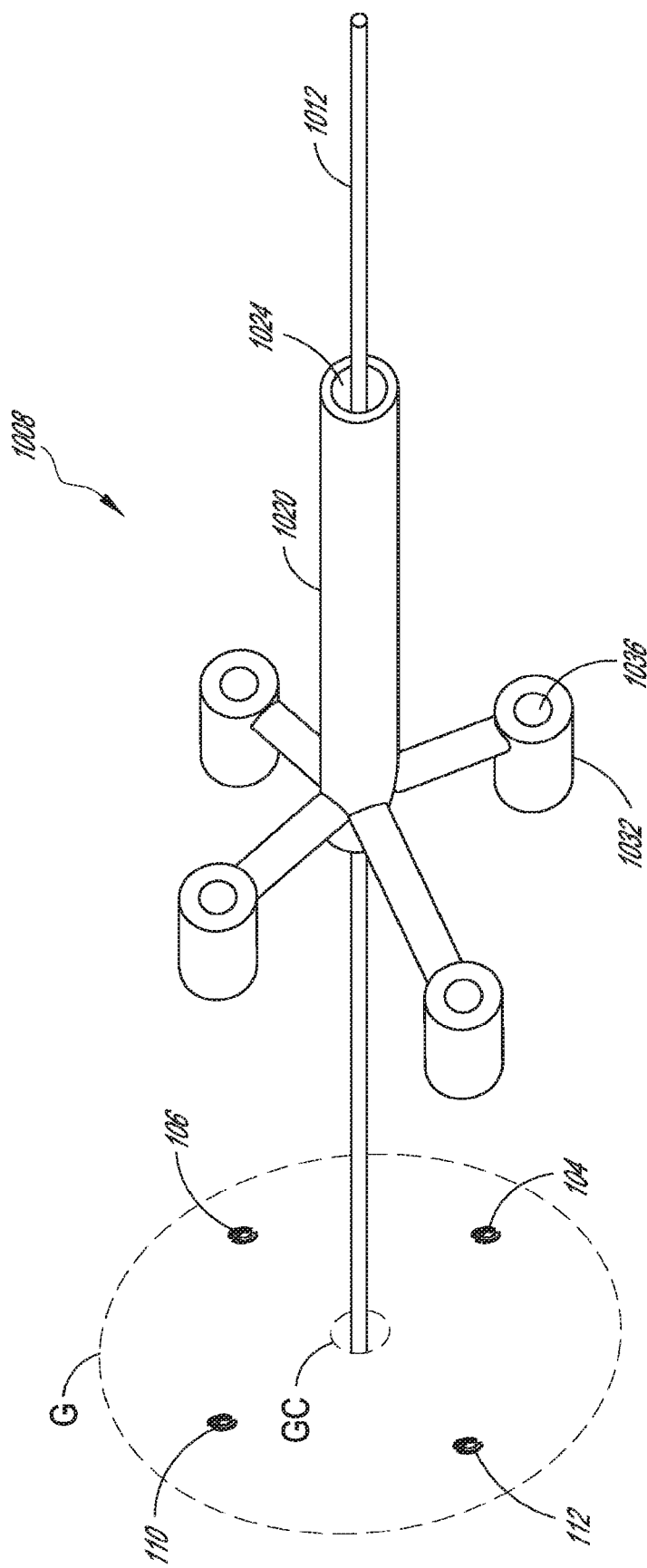
FIG. 19 shows a later step of coupling a patient specific guide with a plurality of reference bushings in a shoulder method.

The foregoing discussion has disclosed apparatuses and methods related to performing ankle surgery. The concepts also can be applied to a shoulder procedure, for example a total shoulder joint replacement. FIGS. 17-19 show an example. In the example a system 1000 is provided that includes the reference bushings 104, 106, 110, 112, a guide 1008, and a central pin 1012. The guide 1008 is configured to guide the placement of the central pin 1012 in a central region of the glenoid G. The guide 1008 has a plurality of arms 1016, e.g., four arms, that extend from a central hub 1020. The hub 1020 has a lumen 1024 extending therethrough to guide the central pin 1012 along an axis defined through the hub 1020 in the center of the lumen 1024. The arms 1016 and other parts of the guide 1008 are formed based on information gathered from the patient, e.g., using an imaging device as discussed above. The arms 1016 each can have a pin guide 1032 disposed at a location away from the central hub 1020. The pin guides 1032 can be hubs or cylindrical bodies. The pin guides 1032 can each have a lumen 1036 therethrough for guiding one of the pins 160 into the glenoid G as discussed below. Each of the guides 1032 can be formed to mate with the proximal portion 122 of one of the reference bushing 104, 106, 110, 112. For example each of the pin guides 1032 can have a convex end portion that can be received in the proximal portion 122 and interface with the concave surface 176.

In a step of a shoulder method, the reference bushings 104, 106, 110, 112 are placed in the scapula. FIG. 18 shows the reference bushings placed in the articular surface of the glenoid G. In many procedures, this surface is subsequently reamed and may be covered by a low friction artificial articular surface. However, the procedure could be modified to place the bushings 104, 106, 110, 112 in the scapula outside the articular area of the glenoid G. FIG. 19 shows the guide 1008 being advanced medially up against the bushings 104, 106, 110, 112. Once the pin guides 1032 come to rest on the bushings 104, 106, 110, 112 the pins 160 can be advanced into the lumens 1036 to secure the guide 1008 in place. Once the guide 1008 is secure, the central pin 1012 can be advanced into the glenoid G and into a central glenoid channel GC. The formation of the glenoid channel GC can be performed through the lumen 1024. Because the guide 1008 is formed with reference to the specific anatomy of the patient the location and the orientation of the glenoid channel GC can be specified by the form of the guide 1008 and the placement of the bushing 104, 106, 110, 112. This can help to more precisely guide other aspects of the procedure such as the trajectory of a reamer, the formation of peripheral holes for anchoring a glenoid component.

In a shoulder replacement procedure, the humerus will generally also be modified. For example, the proximal humerus can be resected and a ball portion can be secured to the humerus to form an anatomic configuration. Or the proximal portion can be resected and a concave member can be supported in the resected humerus by a humeral anchor. The foregoing discussion also discloses how these procedures could be performed using the patient specific techniques disclosed herein. For instance, one or more of the reference bushings 104, 106, 110, 112 can be placed in a side portion of the humerus near the proximal end thereof. The bushings 104, 106, 110, 112 can be used to support a cutting block for resecting the humerus at a position and angle that is specific to the patient and is dictated by the placement of the bushings 104, 106, 110, 112 and the configuration of the cutting block. Also, later aspects of the humeral procedure could also be guided in the methods discussed above. The bushings 104, 106, 110, 112 could be embedded in the resected face of the humerus. Thereafter, a guide similar to the guide 1008 could be used to place a central pin similar to the pin 1012 that could guide further reaming or cutting of the proximal humerus. The central pin could also or alternatively be used to advance a humeral anchor into the proximal humus.

Figure 20:
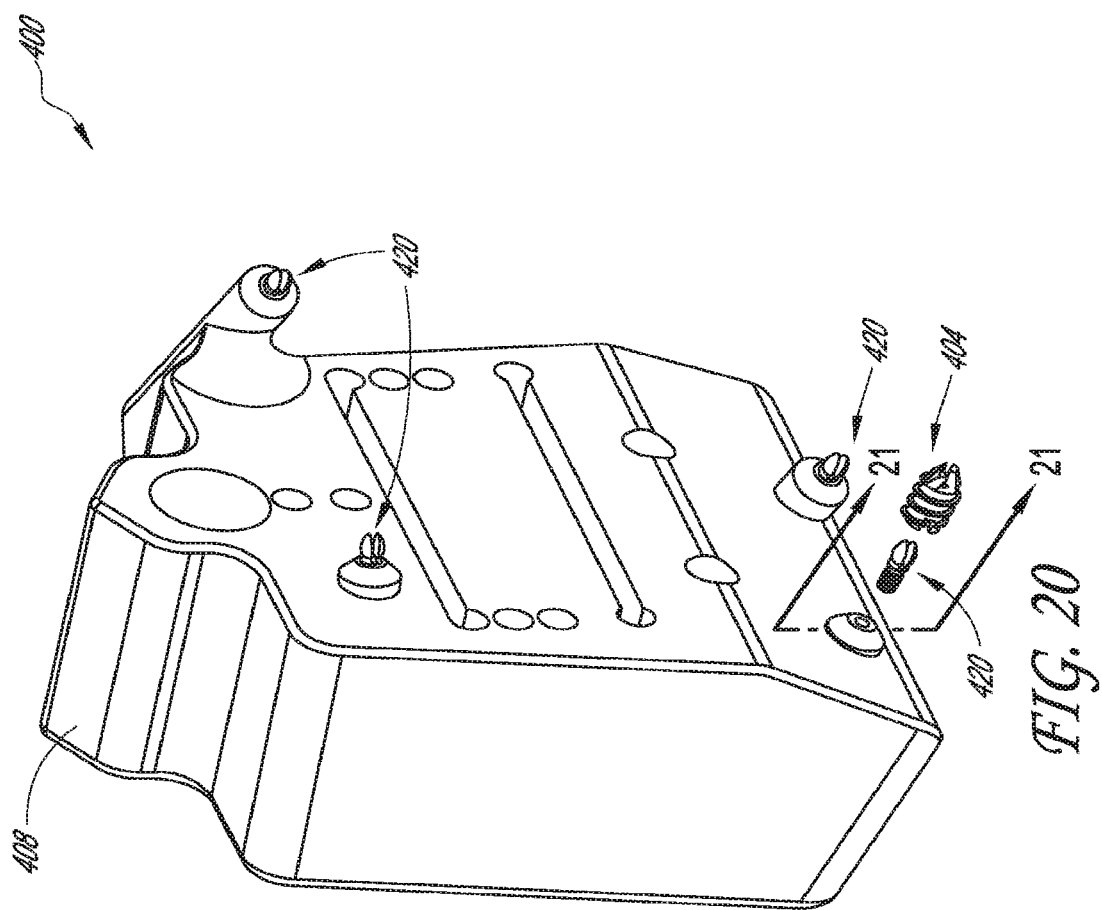
FIG. 20 is a bone preparation system with a snap-fit configuration.

FIGS. 20-23A illustrate a bone system 400 that employs a snap-fit connection between components thereof. The system 400 is similar to the system 100 except as described differently below. The system 400 includes a cutting guide 408, a plurality of deflectable extenders 420 and one or more reference bushings 404. Although one reference bushing 404 is illustrated, the system 400 can have four reference bushings as in the system 100. FIG. 20 shows the cutting guide 408 and one of each of the deflectable extenders 420 and the reference bushings 404 in an exploded configuration. The exploded configuration is provided to better illustrate the components but also shows that in certain embodiments, these components are separate or can be separated in use. The separable configuration allows the user to assemble at least some of the parts at the operating table or in pre-operative activities. The separability of the components also allows at least some of the components to be reused.

FIG. 21 shows components of the system 400 in cross-section illustrating more features of the system 400. A portion of the cutting guide 408 is shown in cross-section. In the section shown, the cutting guide 408 has a lumen 434 that extends through the body of the cutting guide. A portion of the lumen 434 that is closest to the patient when applied to the patient opens into a patient-facing aperture 438. A threaded portion 442 of the lumen 434 is provided from the aperture 438 in a direction away from the aperture into the body of the cutting guide 408. In the illustrated embodiment, the cutting guide 408 also includes a protrusion 446 that extends away from a patient-facing side of the cutting guide 408. The protrusion 446 helps to create clearance, e.g., the gap G discussed above and shown in connection with the system 100 in FIG. 10, between the guide 408 and the tissues of the patient when applied. The protrusion 446 could be smaller or eliminated in some embodiments, for example if the deflectable extenders 420 were elongated sufficiently to provide the gap G.

The threaded portion 442 can be disposed primarily or even exclusively in the protrusion 446. In the illustrated embodiment, the threaded portion 442 also extends into the body of the cutting guide 408.

FIGS. 21 and 23-23A show the deflectable extender 420 in greater detail. The deflectable extender 420 can have a proximal portion 450 and a distal portion 454. The proximal portion 450 has threads 458. The threads 458 are configured to engage the threaded portion 442 of the lumen 434. Although the threads 458 and the threaded portion 442 provide an intuitive, secure connection between the extenders 420 and the cutting guide 408 other structures for such connection could be provided. For example, a bayonet connection or detents could be provided.

The distal portion 454 of the deflectable extender 420 includes a deflectable portion 466. The deflectable portion 466 enables the distal portion 454 to be received in the reference bushing 404 as discussed further below. The distal portion 454 of the deflectable extender 420 has a tapered outer profile 470. The tapered profile 470 can have a generally oval cross-section. In one embodiment, the tapered profile includes two curved surfaces. One curved surface is disposed on a first projection 474 and another curved surfaced is disposed on a second projection 478. The first and second projections 474, 478 can be separated by a gap 482. The gap 482 permits some movement of the projections 474, 478 toward and away from a longitudinal axis 486 of the deflectable extender 420. As discussed further below, the movement of the projections 474, 478 into the gap 482 permits the distal portion 454 to be inserted into and thereafter firmly engage the reference bushing 404 as discussed further below.

While the gap 482 provides for insertion of the deflectable extender 420 into the reference bushing 404 other structures could provide this function as well. For example, the extender 420 could have a detent arrangement or could be compressible such that the extender 420 can be inserted into the reference bushing 404.

The deflectable extender 420 includes a shoulder 480 between the threads 458 and the projections 474, 478. The shoulder 480 provides clearly demarked stop position for the deflectable extender relative to the cutting guide 408. The shoulder 480 allows the surgeon to quickly and accurately advance the deflectable extender 420 to precisely the correct position. This is important in that it helps to maintain the extent of the gap G, which preferably is large enough to allow the tissue beneath the guides to not be disturbed as discussed elsewhere herein.

Figure 22A:
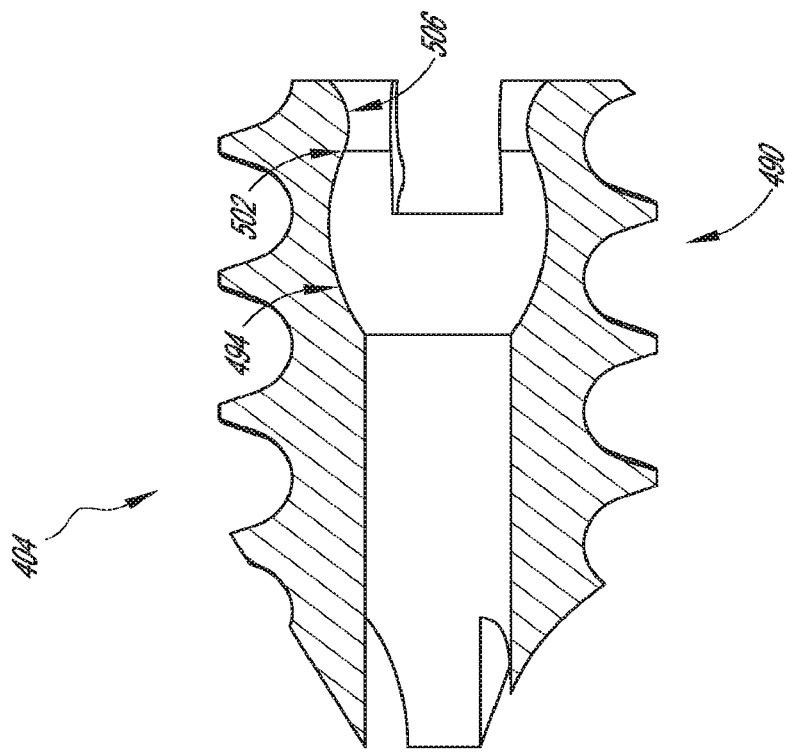
FIG. 22-22A show views of a deflectable extender facilitating a snap-fit configuration.
Figure 22:
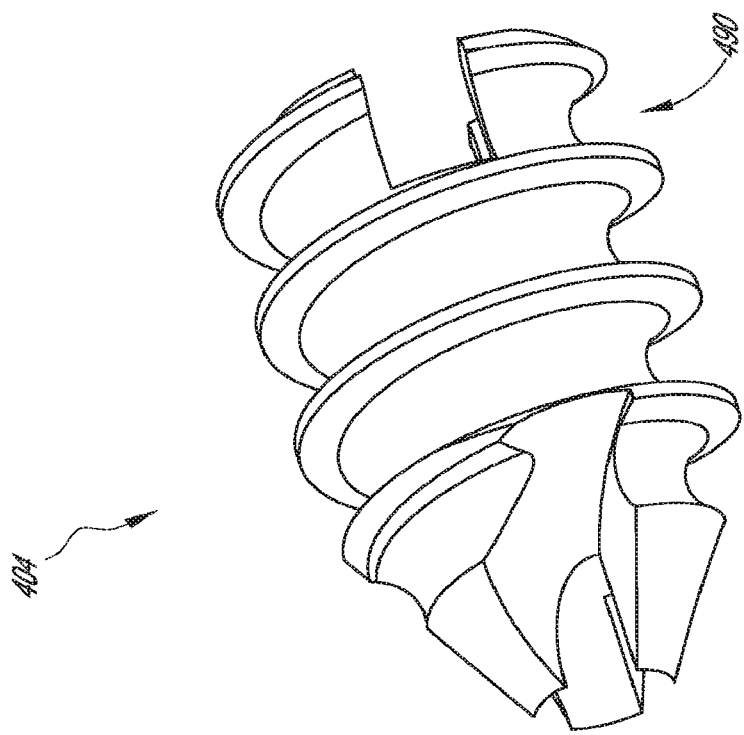

FIGS. 21-22A show details of the reference bushing 404. The reference bushing 404 can be similar to the reference bushing 104 except as described differently below. The reference bushing 404 includes a proximal portion 490 that is configured to receive and retain the distal portion 454 of the deflectable extender 420. The interior surface of the proximal portion 490 can have a surface 494 with an oval curvature, or any curvature that matches the outer tapered profile of the projections 474, 478. In one embodiment, the reference bushing 404 has a constriction 502 between a proximal end of the reference bushing 404 and a distal end of the surface 494. A flared surface 506 extends from the constriction 502 to the proximal end of the reference bushing 404. The constriction 502 can be positioned to be received in a reduced diameter section of the deflectable extender 420 (see FIGS. 23 and 23A). More broadly, the reference bushing 404 and the deflectable extender 420 are configured to have the same shape in cross-section so that a close fit is provided when these components are joined together.

The use of the system 400 is similar to the use of the system 100, except as described differently below. The guide 408 is prepared using patient specific data that can be gathered by any modality, including imaging or mechanical tracing. The reference bushing 404 and any additional reference bushings are implanted as described above in prescribed locations. The deflectable extenders 420 are coupled with the guide 408. In some embodiments, the deflectable extenders are integrated into the guide 408, e.g., pre-assembled or formed as a monolithic structure or of continuous material. Thereafter, the guide 408 and the deflectable extenders 420 are placed on the reference bushings. A distal portion of the profile 474 is placed into the flared surface 506 and rested there. Thereafter, further advancement of the deflectable extenders 420 against the surface 506 moves the projections 474, 478 into the gap 482. This reduces the profile 474 of the distal portion 454 of the extender 420 which allows it to move past the constriction 502. Further advancement disposes the surfaces of the projections 474, 478 against the surface 494. FIG. 21 shows that there is no lumen through the extenders 420 in some embodiments. This is because the snap connection provided between the extenders 420 and the reference bushings 404 (and the other bushings that may be present) is strong enough that the guide 408 need not be secured with separate pins. In other embodiments, the extenders 420 and the guide 408 each have lumens that facilitate placing pins through the cutting guide 408, the extenders 20 and the bushing 404 (and the other bushings that may be present).

The embodiments provided herein provide the additional advantage of allowing for less disruption of the soft tissue and bone around the joint. In particular, the soft tissues do not have to be completely cleared away from the bone surface to mate a patient specific surface with the exposed bone. For example a minimal skin incision may be made to only accommodate the insertion of cutting tools and implant, and the periosteum does not need to be scrapped from the bone. Rather, the reference features can be advanced into contact with discrete, isolated bone references (e.g., reference bushings) while allowing the clearance gap G to be dispose therebetween. The gap G can accommodate soft tissue or can just allow the cutting block not to impinge on the soft tissue or bone therebeneath.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combination or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Thus, it is intended that the scope of at least some of the present inventions herein disclosed should not be limited by the particular disclosed embodiments described above.

What is claimed is:

1. A surgical location preparation system, comprising:
    a first bushing having a distal portion configured to be advanced into a first portion of an anatomical joint;
    a second bushing having a distal portion configured to be advanced into a second portion of the anatomical joint; and
    a patient specific cutting guide having an anterior surface, a posterior surface and at least one internal surface extending from the anterior surface to the posterior surface, the posterior surface having a first bone interface configured to contact the first bushing wherein the first bushing includes a surface configured to limit movement of the patient specific cutting guide, the posterior surface having a second bone interface configured to contact the second bushing wherein the second bushing includes a surface configured to limit movement of the patient specific cutting guide;
    wherein when the patient specific cutting guide is coupled with the first and second bushings a clearance gap is provided between the posterior surface and at least one of the first portion of the anatomical joint and the second portion of the anatomical joint.

2. The surgical location preparation system of claim 1, wherein at least a portion of the posterior surface of the patient specific cutting guide disposed between the first and second bushings is located sufficiently anterior of a posterior end of the first and second bushings that the at least a portion of the posterior surface is out of contact with at least one of the first and the second portions of the anatomical joint.

3. A bone preparation system, comprising:
    a first bushing having a distal portion configured to be advanced into a first portion of a joint;
    a second bushing having a distal portion configured to be advanced into a second portion of a joint; and
    a patient specific cutting guide having an anterior surface, a posterior surface, and at least one surface extending from the anterior surface to the posterior surface, a portion of the posterior surface configured to contact the first bushing wherein the first bushing includes a surface configured to limit movement of the patient specific cutting guide, another portion of the posterior surface configured to contact the second bushing wherein the second bushing includes a surface configured to limit movement of the patient specific cutting guide;
    wherein the first and second portions of the posterior surface are disposed at spaced apart locations such that when the patient specific cutting guide is coupled with the first and second bushings a clearance gap is provided between the posterior surface and at least one of the first portion of the joint and the second portion of the joint.

4. The bone preparation system of claim 3, wherein the locations of the first and second portions of the posterior surface are positioned based on patient anatomy and a desired correction of deformity.

5. The bone preparation system of claim 3, wherein the patient specific cutting guide comprises a first block configured to couple with a tibia and having a first interface portion disposed on a distal surface, the patient specific cutting block comprises a second block configured to couple with a talus and having a second interface portion disposed on a proximal surface, the first and second interface portions configured to mate to provide a spatial position of the tibia and the talus that results in correction of deformity.

6. A surgical method, comprising:
    providing a first bushing having a distal portion configured to be advanced into a first portion of an ankle joint, a second bushing having a distal portion configured to be advanced into a second portion of an ankle joint and a patient specific cutting guide having an anterior surface, a posterior surface, and at least one surface extending from the anterior surface to the posterior surface, a portion of the posterior surface configured to contact the first bushing wherein the first bushing includes a surface configured to limit movement of the patient specific cutting guide, another portion of the posterior surface configured to contact the second bushing wherein the second bushing includes a surface configured to limit movement of the patient specific cutting guide; wherein the first and second portions of the posterior surface are disposed at spaced apart locations;
    advancing the first bushing into a tibia adjacent to the ankle joint of a patient;
    advancing the second bushing into a talus adjacent to the ankle joint;
    after advancing the first bushing into the tibia and the second bushing into the talus, obtaining the location and orientation of the first and second bushings relative to a portion of the tibia around the first and second bushings and a portion of the talus around the second bushing;
    and in surgery connecting the patient specific cutting guide to the first bushing and to the second bushing;
    wherein the first and second bushings are coupled to the patient specific cutting guide at locations based upon the location and orientation information; and
    wherein when the patient specific cutting guide is coupled to the patient, a gap is provided between the patient specific guide and at least one of the tibia and the talus.

7. The surgical method of claim 6 wherein one of at least the first bushing and the second bushing have a smooth tapered distal portion.

8. The surgical method of claim 6 wherein the first and second bushings are secured in the bone by at least one of threads and an interference fit.

9. The surgical method of claim 6, further comprising advancing a third bushing into the tibia and advancing a fourth bushing into the talus.

10. The surgical method of claim 6 wherein obtaining the location and orientation information comprises performing a CT scan after the bushings are advanced into the tibia and into the talus.

11. The surgical method of claim 6, wherein the patient specific cutting guide is configured to contact the first bushing when the second bushing is advanced into the talus, and wherein when the patient specific cutting guide is connected to the bushings, a posterior surface of the patient specific cutting guide does not contact the tibia or the talus.

12. The surgical method of claim 6, wherein when the patient specific cutting guide contacts the first and second bushings, the patient specific cutting guide only contacts the first and second bushings in the absence of contact with the tibia or the talus.

13. The surgical method of claim 6, wherein when the patient specific cutting guide contacts the first and second bushings, the patient specific cutting guide is spaced apart from the tibia.

14. The surgical method of claim 6, wherein when the patient specific cutting guide contacts the first and second bushings the patient specific cutting guide is spaced apart from the talus.

15. The surgical method of claim 6, further comprising cutting the tibia and/or the talus using patient specific cutting guide to prepare the tibia and/or the talus to receive an ankle prosthesis.

16. The surgical method of claim 15, further comprising coupling an ankle prosthesis to the tibia and the talus after the tibia and/or talus have/has been cut.

17. The surgical method of claim 6, further comprising modifying connective tissue around the ankle joint in association with correction of deformities in the ankle.

18. The surgical method of claim 6, further comprising:
    placing a first cannula through a first incision such that a distal end of the first cannula is adjacent to the anterior surface of the tibia and a proximal end of the first cannula is outside of the skin of the patient;
    placing a second cannula through a second incision such that a distal end of the second cannula is adjacent to the neck of the talus and a proximal end of the second cannula is outside of the skin of the patient;
    advancing the first bushing through the first cannula; and
    advancing the second bushing through the second cannula.

19. The surgical method of claim 6, placing ankle joint in plantar flexion and rigidly connecting the patient specific cutting guide to the talus.

20. The surgical method of claim 19, wherein coupling the patient specific cutting guide to the first bushing comprises rotating the ankle joint out of plantar flexion after the patient specific cutting guide is rigidly attached to the talus.

21. The surgical method of claim 6, further comprising creating the patient specific guide based on the location and orientation of information.

22. A surgical method, comprising:
    providing a first bone reference having a distal portion configured to be advanced on or in a first bone surface adjacent to a joint of a patient;
    providing a second bone reference having a distal portion configured to be advanced on or in a second bone surface adjacent to the joint of the patient;
    coupling a first reference surface of a patient specific cutting guide with the first bone reference after providing the first bone reference; and
    coupling a second reference surface the patient specific cutting guide with the second bone reference after providing the second bone reference such that a portion of the first reference surface is configured to contact the first bone reference wherein the first bone reference includes a surface configured to limit movement of the patient specific cutting guide, and further wherein another portion of the first reference surface is configured to contact the second bone reference wherein the second bone reference includes a surface configured to limit movement of the patient specific cutting guide;
    wherein the coupling steps can be performed without disrupting the soft tissue or bone adjacent to the joint.

23. The method of claim 22, wherein when the first reference feature is coupled with the first bone reference and the second reference feature is coupled with the second bone reference, a surface defined between the first and second reference features and facing the bone is spaced from the bone sufficiently to accommodate soft tissue or bone to reduce dissection of such soft tissues and bone.

* * * * *